(12) United States Patent
Herr et al.

(10) Patent No.: US 7,279,009 B2
(45) Date of Patent: *Oct. 9, 2007

(54) SPEED-ADAPTIVE AND PATIENT-ADAPTIVE PROSTHETIC KNEE

(75) Inventors: Hugh M. Herr, Somerville, MA (US); Ari Wilkenfeld, Cleveland Heights, OH (US); Olaf Bleck, Chelsea, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/646,097

(22) Filed: Aug. 22, 2003

(65) Prior Publication Data

US 2004/0039454 A1    Feb. 26, 2004

Related U.S. Application Data

(63) Continuation of application No. 09/823,931, filed on Mar. 29, 2001, now Pat. No. 6,610,101.

(60) Provisional application No. 60/192,966, filed on Mar. 29, 2000.

(51) Int. Cl.
*A61F 2/64* (2006.01)
*A61F 2/68* (2006.01)

(52) U.S. Cl. ............................ 623/44; 623/39; 623/43

(58) Field of Classification Search .................... None
See application file for complete search history.

(56) References Cited

U.S. PATENT DOCUMENTS 3,820,168 A   6/1974   Horvath

| | | |
|---|---|---|
| 3,995,324 A | 12/1976 | Burch |
| 4,005,496 A | 2/1977 | Wilkes |
| 4,064,569 A | 12/1977 | Campbell |
| 4,065,815 A | 1/1978 | Sen-Jung |
| 4,209,860 A | 7/1980 | Graupe |
| 4,212,087 A | 7/1980 | Mortensen |

(Continued)

FOREIGN PATENT DOCUMENTS

DE    35 43 291 A1    6/1987

(Continued)

OTHER PUBLICATIONS

Otto Bock Orthopadische Industrie, *C-LEG A new dimension in amputee mobility*, Otto Bock 1997.

(Continued)

*Primary Examiner*—David Willse
*Assistant Examiner*—Javier G. Blanco
(74) *Attorney, Agent, or Firm*—Knobbe, Martens, Olson & Bear, LLP

(57) ABSTRACT

The invention relates to an automated speed-adaptive and patient-adaptive control scheme and system for a knee prosthesis. The control scheme and system utilizes sensory information measured local to the prosthesis to automatically adjust stance and swing phase knee resistances to a particular wearer under a wide variety of locomotory activities. Advantageously, no patient-specific information needs to be pre-programmed into the prosthetic knee by a prosthetist or the patient. The system is able to adapt to various types of disturbances once the patient leaves the prosthetist's facility because it is patient-adaptive and speed-adaptive.

28 Claims, 11 Drawing Sheets

U.S. PATENT DOCUMENTS

| | | | |
|---|---|---|---|
| 4,310,932 A | 1/1982 | Näder et al. | |
| 4,569,352 A | 2/1986 | Petrofsky et al. | |
| 4,685,927 A | 8/1987 | Haupt | |
| 4,711,242 A | 12/1987 | Petrofsky | |
| 4,711,450 A | 12/1987 | McArthur | |
| 4,760,850 A | 8/1988 | Phillips et al. | |
| 4,790,522 A | 12/1988 | Drutchas | |
| 4,854,428 A | 8/1989 | Horvath | |
| 4,876,944 A | 10/1989 | Wilson et al. | |
| 4,893,648 A | 1/1990 | Horvath | |
| 4,919,418 A | 4/1990 | Miller | |
| 4,958,705 A | 9/1990 | Horvath | |
| 5,062,856 A | 11/1991 | Sawamura et al. | |
| 5,092,902 A | 3/1992 | Adams et al. | |
| 5,133,774 A | 7/1992 | Sawamura et al. | |
| 5,181,931 A | 1/1993 | van de Veen | |
| 5,197,488 A | 3/1993 | Kovacevic | |
| 5,201,772 A | 4/1993 | Maxwell | |
| 5,230,672 A | 7/1993 | Brown et al. | |
| 5,277,281 A * | 1/1994 | Carlson et al. | 188/267 |
| 5,284,330 A | 2/1994 | Carlson et al. | |
| 5,336,269 A | 8/1994 | Smits | |
| 5,383,939 A | 1/1995 | James | |
| 5,397,287 A | 3/1995 | Lindfors | |
| 5,398,917 A | 3/1995 | Carlson et al. | |
| 5,405,409 A | 4/1995 | Knoth | |
| 5,413,611 A | 5/1995 | Haslam, II et al. | |
| 5,443,521 A | 8/1995 | Knoth et al. | |
| 5,472,412 A | 12/1995 | Knoth | |
| 5,476,441 A | 12/1995 | Durfee et al. | |
| 5,545,232 A | 8/1996 | Van de Veen | |
| 5,571,205 A | 11/1996 | James | |
| 5,645,590 A | 7/1997 | van de Veen | |
| 5,645,752 A | 7/1997 | Weiss et al. | |
| 5,670,077 A | 9/1997 | Carlson et al. | |
| 5,683,615 A | 11/1997 | Munoz | |
| 5,704,945 A | 1/1998 | Wagner et al. | |
| 5,711,746 A * | 1/1998 | Carlson | 482/112 |
| 5,728,170 A | 3/1998 | Becker et al. | |
| 5,728,174 A | 3/1998 | Fitzlaff | |
| 5,746,774 A | 5/1998 | Kramer et al. | |
| 5,749,533 A | 5/1998 | Daniels | |
| 5,755,813 A | 5/1998 | Krukenberg | |
| 5,823,309 A | 10/1998 | Gopalswamy et al. | |
| 5,842,547 A | 12/1998 | Carlson et al. | |
| 5,888,212 A | 3/1999 | Petrofsky et al. | |
| 5,888,236 A | 3/1999 | van de Veen | |
| 5,893,891 A | 4/1999 | Zahedi | |
| 5,900,184 A | 5/1999 | Weiss et al. | |
| 5,906,767 A | 5/1999 | Karol et al. | |
| 5,947,238 A | 9/1999 | Jolly et al. | |
| 5,948,021 A | 9/1999 | Radcliffe | |
| 5,955,667 A | 9/1999 | Fyfe | |
| 5,957,981 A | 9/1999 | Gramnäs | |
| 5,960,918 A | 10/1999 | Moser et al. | |
| 5,967,273 A | 10/1999 | Hampton | |
| RE36,521 E | 1/2000 | Hiemisch | |
| 6,027,664 A | 2/2000 | Weiss et al. | |
| 6,095,486 A | 8/2000 | Ivers et al. | |
| 6,113,642 A | 9/2000 | Petrofsky et al. | |
| 6,117,177 A | 9/2000 | Chen et al. | |
| 6,139,586 A | 10/2000 | Wagner et al. | |
| 6,168,634 B1 | 1/2001 | Schmitz | |
| 6,301,964 B1 | 10/2001 | Fyfe et al. | |
| 6,352,144 B1 * | 3/2002 | Brooks | 188/267.2 |
| 6,423,098 B1 | 7/2002 | Biedermann | |
| 6,443,993 B1 | 9/2002 | Koniuk | |
| 6,513,381 B2 | 2/2003 | Fyfe et al. | |
| 6,517,585 B1 | 2/2003 | Zahedi et al. | |
| 6,679,920 B2 | 1/2004 | Biedermann et al. | |
| 6,719,806 B1 | 4/2004 | Zahedi et al. | |
| 6,740,125 B2 * | 5/2004 | Mosler | 623/45 |
| 6,755,870 B1 | 6/2004 | Biedermann et al. | |
| 6,764,520 B2 * | 7/2004 | Deffenbaugh et al. | 623/24 |
| 2001/0029400 A1 | 10/2001 | Deffenbaugh et al. | |
| 2004/0217324 A1 * | 11/2004 | Hsu et al. | 252/62.52 |

FOREIGN PATENT DOCUMENTS

| | | |
|---|---|---|
| DE | 4305213 A1 | 8/1993 |
| DE | 4318901 A1 | 1/1994 |
| DE | 4229330 A1 | 3/1994 |
| EP | 0 549 855 B1 | 9/1992 |
| EP | 0503775 A1 | 9/1992 |
| EP | 0628296 A2 | 12/1994 |
| EP | 0 957 838 B1 | 11/1999 |
| EP | 1 066 793 A2 | 1/2001 |
| EP | 1125825 A2 | 8/2001 |
| FR | 2623086 A1 | 5/1989 |
| GB | 2201260 A | 8/1988 |
| GB | 2 328 160 A | 8/1998 |
| GB | 2 334 891 A | 3/1999 |
| GB | 2 338 653 A | 12/1999 |
| GB | 2244006 A | 11/2001 |
| JP | 60-81530 A | 5/1985 |
| JP | 3-81633 A | 8/1991 |
| JP | 3-181633 A | 8/1991 |
| JP | 4-78337 A | 3/1992 |
| WO | WO 96/41599 | 6/1996 |
| WO | WO 99/29272 | 12/1998 |
| WO | WO 99/08621 | 2/1999 |
| WO | WO 99/44547 | 9/1999 |
| WO | WO 00/38599 | 7/2000 |
| WO | WO 02/080825 A2 | 10/2002 |

OTHER PUBLICATIONS

*Biologically Inspired Autoadaptive Control of a Knee Prosthesis*, Ari J. Wilkenfeld, Ph.D. Dissertation, Massachusetts Institute of Technology, pp. 1-106, Sep. 2000.

An Auto-Adaptive External Knee Prosthesis, Ari Wilkenfeld & Hugh Herr, Artifical Intelligence Laboratory, MIT, Cambridge, Massachusetts, 3 pages, Sep. 2000.

Biologically inspired autoadaptive control of a knee prosthesis, Ari Wilkenfeld, Ph.D., Dissertation Abstract, MIT, Cambridge, Massachusetts, 1 page, Sep. 2000.

"State-of-the-Art Prosthetic Leg Incorporates Magneto-Rheological Technology" Medical Product Manufacturing News, Nov. 2000.

Donald L. Grimes, "An Active Multi-Mode Above-Knee Prosthesis Controller," Massachusetts Institute of Technology 1979, 158 pages.

Otto Bock—The Electronic C-Leg Knee Joint System, Instructions for Use, 2002.

Otto Bock—The Electronic C-Leg compact Leg Prosthesis System, Instructions for Use, 2002.

* cited by examiner

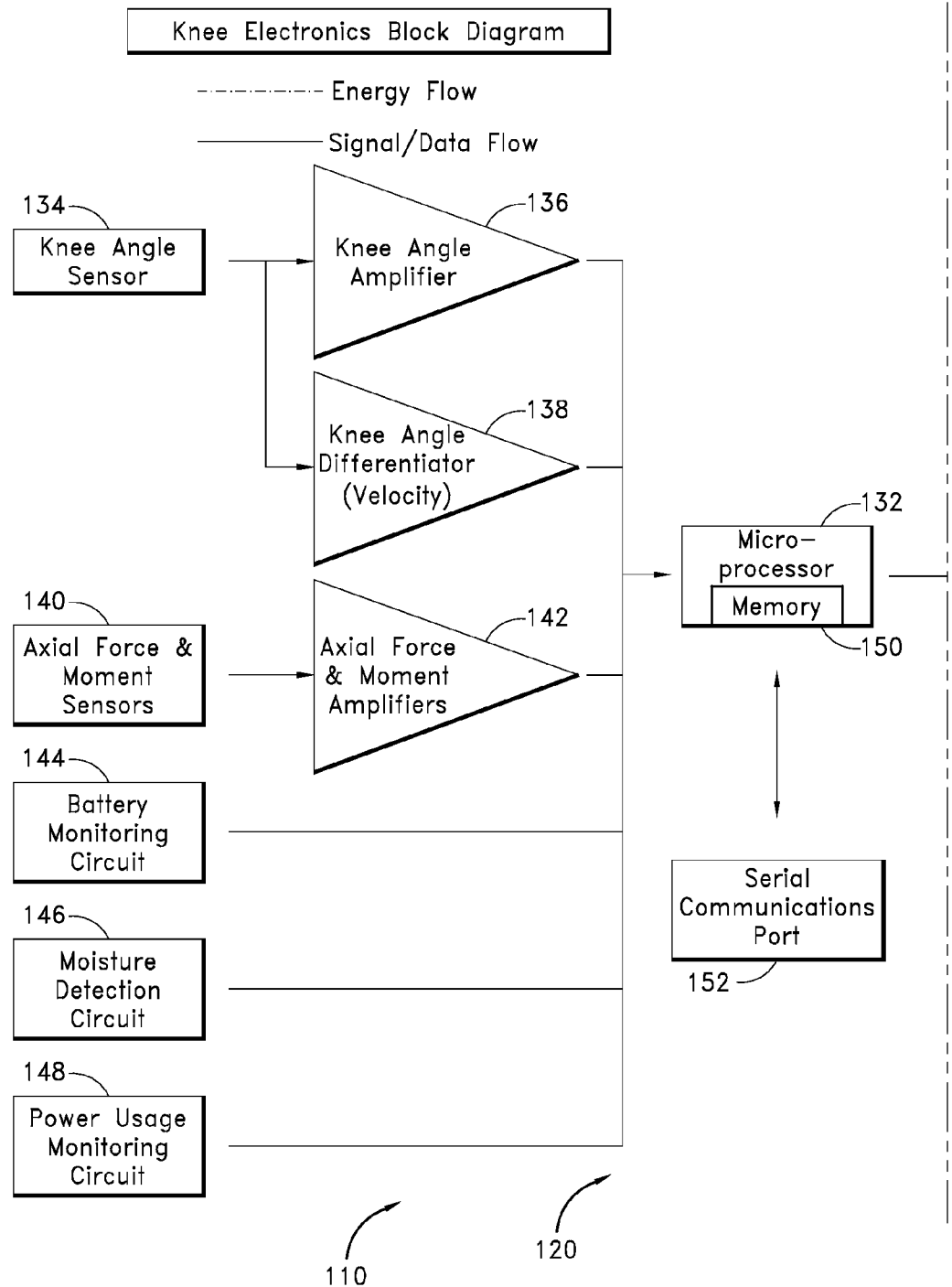

SPEED-ADAPTIVE AND PATIENT-ADAPTIVE PROSTHETIC KNEE

RELATED APPLICATIONS

This application is a continuation of U.S. application Ser. No. 09/823,931, filed Mar. 29, 2001, now U.S. Pat. No. 6,610,101 B2, which claims the benefit of U.S. Provisional Application No. 60/192,966, filed Mar. 29, 2000, the entirety of each one of which is hereby incorporated by reference herein.

BACKGROUND OF THE INVENTION

1. Field of the Invention

The present invention relates to prosthetic knees in general and, in particular, to a speed-adaptive and patient-adaptive control scheme and system for an external knee prosthesis.

2. Description of the Related Art

Most conventional active knee prostheses are variable torque brakes where joint damping is controlled by a microprocessor as an amputee walks from step to step. Many brake technologies have been employed for knees including pneumatic, hydraulic and magnetorheological.

With most current prosthetic technology, a prosthetist adjusts knee resistances to tune the artificial leg to the amputee so that the knee prosthesis moves naturally at slow, moderate and fast walking speeds. During use, sensors local to the prosthesis are used to detect walking speed. A microprocessor then adjusts knee resistances based on customized values or data previously programmed by the prosthetist for that specific patient only.

Disadvantageously, such a methodology for programming a prosthetic knee is time consuming for both the prosthetist and the patient and has to be repeated for each patient. Moreover, any unforeseen changes in the patient or in the patient's environment are not compensated for by the knee prosthesis after the patient has left the prosthetist's facility. This lack of adaptiveness in the knee system can disrupt normal locomotion and render the pre-programmed knee uncomfortable or even unsafe. In this situation, the patient must return to the prosthetist's facility for the knee prosthesis to be reprogrammed. Again, undesirably this results in additional wastage of time and further adds to the cost.

SUMMARY OF THE INVENTION

Accordingly it is one advantage of the present invention to overcome some or all of the above limitations by providing an automated speed-adaptive and patient-adaptive control scheme and system for a knee prosthesis. The control scheme and system utilizes sensory information measured local to the prosthesis to automatically adjust stance and swing phase knee resistances to a particular wearer under a wide variety of locomotory activities. Advantageously, no patient-specific information needs to be pre-programmed into the prosthetic knee by a prosthetist or the patient. The system is able to adapt to various types of disturbances once the patient leaves the prosthetist's facility because it is patient-adaptive and speed-adaptive.

In accordance with one preferred embodiment, a method is provided of adaptively controlling the stance phase damping of a prosthetic knee worn by a patient. The method comprises the step of providing a memory in the prosthetic knee. The memory has stored therein correlations between sensory data and stance phase damping established in clinical investigations of amputees of varying body size. Instantaneous sensory information is measured using sensors local to the prosthetic knee as the patient stands, walks or runs. The instantaneous sensory information is used in conjunction with the correlations to automatically adjust stance phase damping suitable for the patient without requiring patient specific information to be pre-programmed in the prosthetic knee.

In accordance with another preferred embodiment, a method is provided of adaptively controlling the swing phase damping torque of a prosthetic knee worn by a patient as the patient travels at various locomotory speeds. The ground contact time of a prosthetic foot connected to the prosthetic knee by a prosthetic leg is indicative of the locomotory speed of the patient. The method comprises the step of continuously measuring the contact time over periods of one gait cycle as the patient ambulates at various locomotory speeds. The contact time is stored within a memory of the prosthetic knee in time slots corresponding to the locomotory speed of the patient. The swing phase damping for knee flexion is iteratively modulated to achieve a target peak flexion angle range until the flexion damping converges within each time slot. The swing phase damping for knee extension is iteratively modulated to control the impact force of the extending prosthetic leg against an artificial knee cap of the prosthetic knee until the extension damping converges within each time slot. The converged damping values are used to automatically control swing phase damping at all locomotory speeds.

In accordance with one preferred embodiment, an adaptive prosthetic knee is provided for controlling the knee damping torque during stance phase of an amputee. The prosthetic knee generally comprises a controllable knee actuator, sensors and a controller. The knee actuator provides a variable damping torque in response to command signals. The sensors measure the force and moment applied to the prosthetic knee as the amputee moves over a supporting surface. The controller has a memory and is adapted to communicate command signals to the knee actuator and receive input signals from the sensors. The memory has stored therein relationships between sensory data and stance phase damping established in prior clinical investigations of patients of varying body size. The controller utilizes sensory data from the sensors in conjunction with the relationships to adaptively and automatically control the damping torque provided by the knee actuator during stance phase independent of any prior knowledge of the size of the amputee.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

In order for a trans-femoral (above-knee) amputee to walk in a variety of circumstances, a prosthetic knee should provide stance control to limit buckling when weight is applied to the limb. In addition, a prosthesis should provide swing phase control so that the knee reaches full extension just prior to heel strike in a smooth and natural manner.

Unlike a biological knee, a prosthetic knee should accomplish both stance and swing control without direct knowledge of its user's intent or of the environment. Rather, a prosthetic knee has to infer whether the amputee is walking, running, or sitting down. It should also determine when subtle or drastic changes occur in the environment, such as when the user lifts a suitcase or walks down a slope. Still further, the prosthesis should move naturally and be safe at all locomotory speeds, and should perform equally well for all amputees, independent of body weight, height, or activity level, without requiring patient-specific information or programming from a prosthetist.

In accordance with one preferred embodiment of the present invention, a prosthetic knee is precisely and accurately controlled at substantially all locomotory speeds and for substantially all patients. The invention utilizes an adaptation scheme that automatically adjusts stance and swing resistances or damping without pre-programmed information from a patient or prosthetist, making the "smart" knee both speed-adaptive and patient-adaptive.

Normal Level-Ground Ambulation

Understanding normal human walking/running provides the basis for the design and development of effective lower limb prostheses with controlled motion. Normal human locomotion or gait can be described as a series of rhythmical alternating movements of the limbs and trunk which result in the forward progression of the body's center of gravity.

Figure 1:
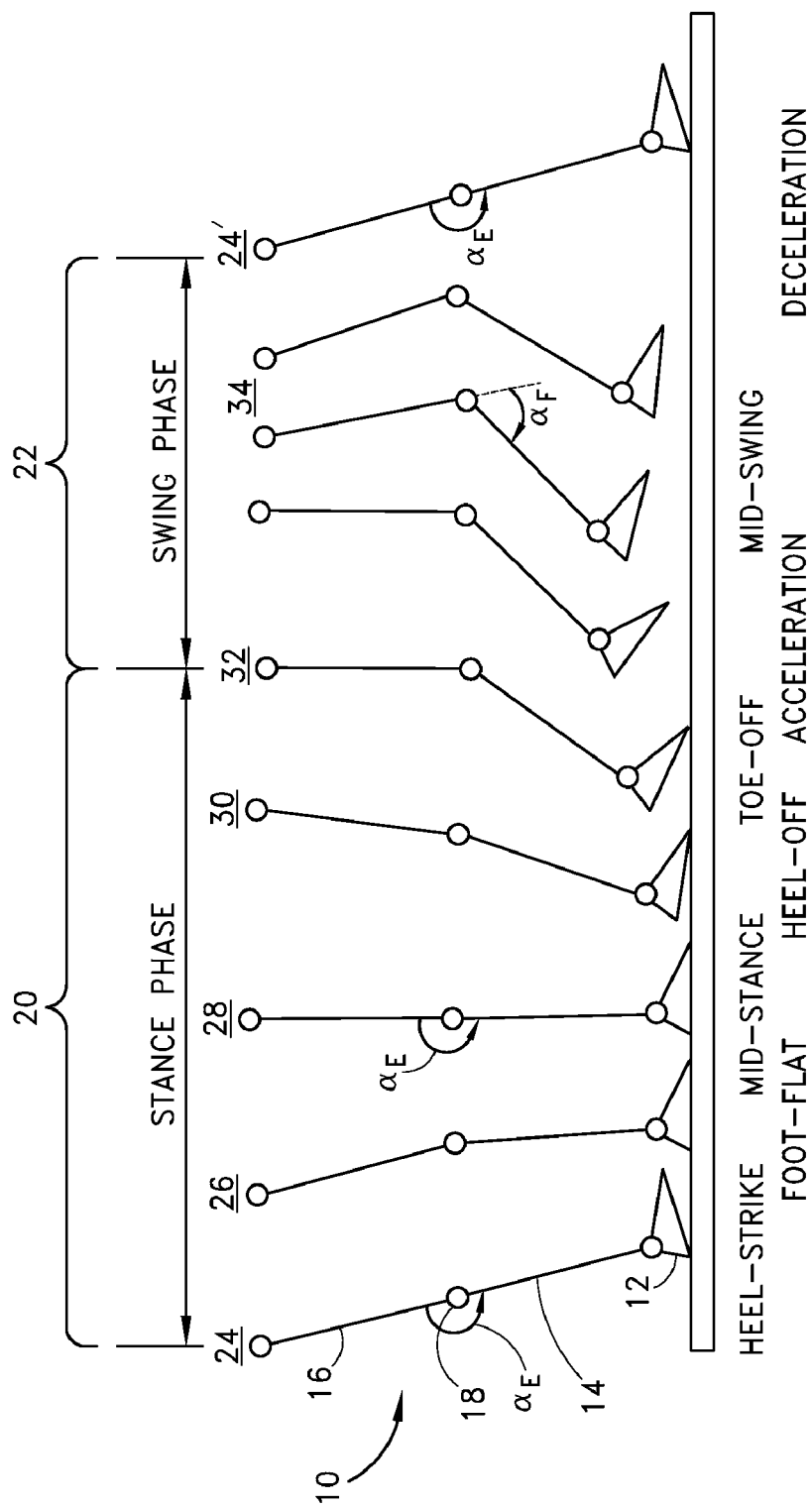
FIG. 1 is a schematic drawing of one normal human locomotion cycle illustrating the various limb positions during stance and swing phases.

One typical normal level-ground gait cycle, as schematically depicted in FIG. 1, comprises of the activity that occurs between heel strike of one lower limb 10 and the subsequent heel strike of the same limb 10. The limb or leg 10 generally comprises a foot 12 and a shin or shank portion 14 coupled or articulated to a thigh portion 16 via a knee or knee joint 18. During a single gait cycle each lower limb or extremity passes through one stance or extended phase 20 and one swing phase 22.

The stance phase 20 begins at heel-strike 24 when the heel touches the floor or supporting ground surface and the stance knee begins to flex slightly. This flexion allows for shock absorption upon impact and also maintains the body's center of gravity at a more constant vertical level during stance.

Shortly after heel-strike 24, the sole makes contact with the ground at the beginning of the foot-flat phase 26. After maximum flexion is reached in the stance knee, the joint begins to extend again, until maximum extension is reached at mid-stance 28 as the body weight is swung directly over the supporting extremity and continues to rotate over the foot.

As the body mass above the ankle continues to rotate forward, the heel lifts off the ground at heel-off 30. Shortly after this, the body is propelled forward by the forceful action of the calf-muscles powered plantar-flexion). The powered plantar-flexion phase terminates when the entire foot rises from the ground at toe-off 32.

During late stance, the knee of the supporting leg flexes in preparation for the foot leaving the ground for swing. This is typically referred to in the literature as "knee break". At this time, the adjacent foot strikes the ground and the body is in "double support mode", that is, both the legs are supporting the body weight.

At toe-off 32, as the hip is flexed and the knee reaches a certain angle at knee break, the foot leaves the ground and the knee continues to flex into the swing phase. During early swing the foot accelerates. After reaching maximum flexion at mid-swing 34, the knee begins to extend and the foot decelerates. After the knee has reached full extension, the foot once again is placed on the ground at heel-strike 24' and the next walking cycle begins.

Typically, the anatomical position is the upright position, therefore flexion is a movement of a body part away from the extended or stance or anatomical position. Thus, bending of the knee is knee flexion. Extension is a movement of a limb towards the anatomical position, thus knee extension is a movement in the "straightening" direction.

Stated differently, if a knee joint is looked at as a simple hinge, there are two separate actions which can occur. In "flexion", the knee joint rotates to enable the upper and lower leg segments to move closer together. In "extension" the knee joint rotates in the opposite direction, the leg segments move apart and the leg straightens.

During a typical normal walking progression on a generally level surface, the maximum flexion angle $\alpha_F$ varies between about 60° and 80°. The maximum extension angle $\alpha_E$ is typically about or close to 180°. Thus, in level walking the normal human knee rotates through a range of approximately 60°-80° going from a position of full extension in late stance to 60°-80° of flexion shortly after toe-off. In other situations, for example, in a sitting position, the maximum flexion angle $\alpha_F$ can be about 140°-150°.

Figure 2:
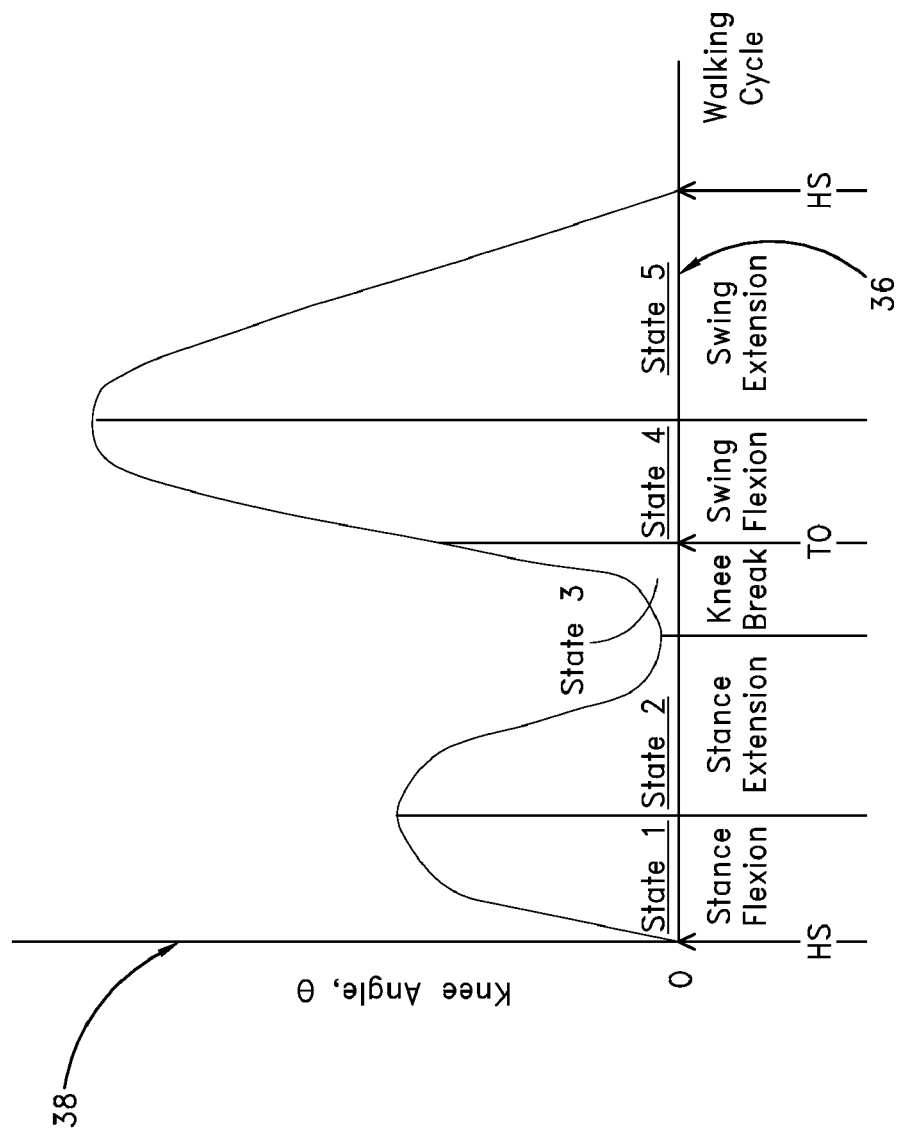
FIG. 2 is a schematic graphical representation of the variation in knee angle showing state transitions during one normal gait cycle.

Referring to FIG. 2, preferably, the gait cycle of FIG. 1 is categorized into five distinct states or phases. FIG. 2 schematically shows the knee angle θ, that is, the angle the knee rotates from full extension, with state or phase transitions during activity that occurs between the heel strike (HS) of one lower limb and the subsequent heel strike (HS) of the same limb. The x-axis 36 represents time between consecutive heel strikes of the walking cycle. The y-axis 38 represents the knee angle θ.

State 1 represents early stance flexion just after heel strike (HS). State 2 represents early or mid stance extension after maximum stance flexion is reached in State 1. State 3, or knee break, typically occurs at the end of stance, beginning just after the knee has fully extended and terminates when the foot has left the ground at toe-off (TO). State 4 represents a period of knee flexion during the swing phase of a walking or running cycle. State 5 represents a period of knee extension during the swing phase of a walking or running cycle, after maximum swing flexion is reached in State 4.

As discussed later herein, these basic states or phases suggest the framework of a prosthetic knee controller as a state machine. Thus, FIG. 2 is a graphical representation of a person moving through a normal gait cycle and the location of each state within that cycle. Table 1 below summarizes the activity during each of the States 1 to 5.

TABLE 1

| State | Activity |
| --- | --- |
| 1 | Stance Flexion |
| 2 | Stance Extension |
| 3 | Knee Break |
| 4 | Swing Flexion |
| 5 | Swing Extension |

Figure 3:
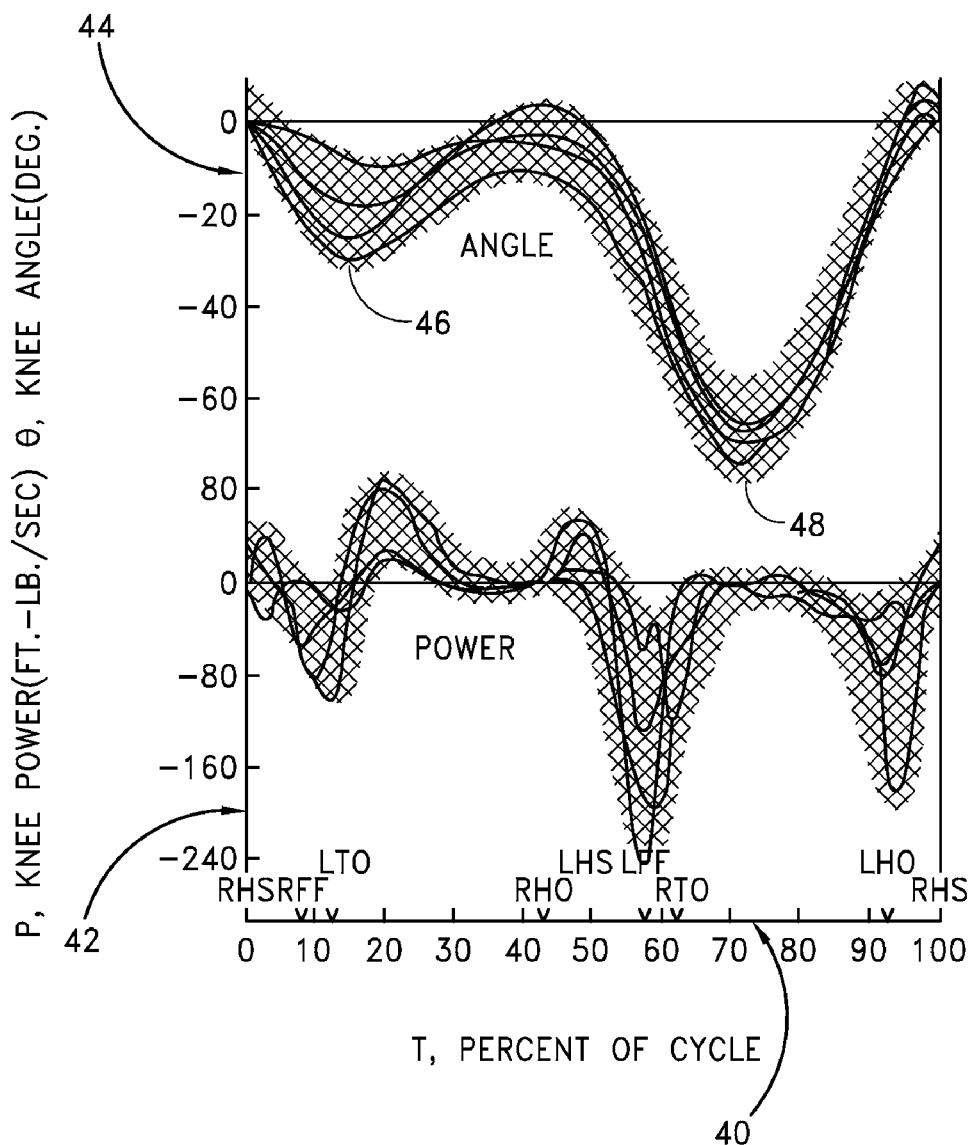
FIG. 3 is a plot of biological knee angle and mechanical power against percentage of a complete walking cycle for one subject.

FIG. 3 is a plot of typical biological knee angle and knee power versus time normalized to the step period (adapted from Grimes, 1979). The x-axis 40 represents time normalized to the step period, T, or percentage of walking cycle. The y-axis 42 represents knee power (P in ft-lb/sec) and the y-axis 44 represents knee angle (θ in degrees).

In FIG. 3, four walking trials are shown for one subject. Zero percent and one hundred percent mark two consecutive heel strikes of the same leg and zero angle generally corresponds to the heel strike angle. Also, in FIG. 3, RHS represents right heel strike, RFF represents right flat foot, LTO represents left toeoff, RHO represents right heel off. LHS represents left heel strike, LFF represents left flat foot, RTO represents right toe off and LHO represents left heel off.

Still referring to FIG. 3, the smaller dip 46 in the angle plot (about 15% of the full cycle) represents the flexion and extension of the knee during early or mid stance, whereas the larger dip 48 (about 75% of the full cycle) represents the flexion and extension of the knee during swing phase. Throughout the cycle, the knee mechanical power is primarily negative or dissipative. This justifies the use or employment of a variable damper or a variable torque brake in the knee prosthesis. Such a variable damper or knee actuator is discussed further herein below.

System Configuration

Figure 4:
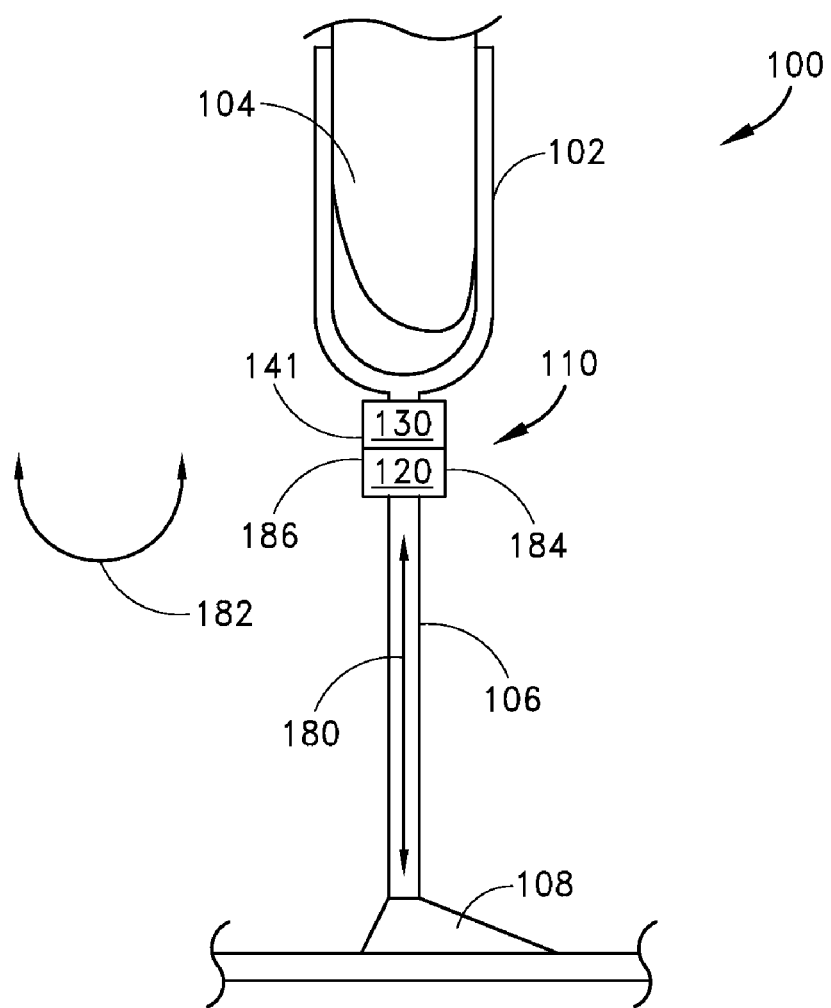
FIG. 4 is a schematic illustration of a lower limb prosthetic assembly comprising an electronically controlled prosthetic knee and having features and advantages in accordance with one preferred embodiment of the present invention.

FIG. 4 is a schematic illustration of a lower limb prosthetic assembly or prosthesis 100 comprising an electronically controlled active knee prosthesis 110 and having features and advantages in accordance with one preferred embodiment of the present invention. As described in greater detail later herein, preferably, the active knee prosthesis comprises a variable-torque braking system or damper 130 and an onboard control unit or system 120 housed in a supporting frame 141. The prosthetic knee system 110 provides resistive forces to substantially simulate the position and motion of a natural knee joint during ambulation and/or other locomotory activities performed by the amputee.

At one end the artificial knee system 110 is coupled or mechanically connected to a residual limb socket 102 which receives a residual limb, stump or femur portion 104 of the amputee. The other end of the prosthetic knee 110 is coupled or mechanically connected to a pylon, shin or shank portion 106 which in turn is coupled or mechanically connected to a prosthetic or artificial foot 108.

Advantageously, the prosthetic knee system 110 of the preferred embodiments is both speed-adaptive and patient-adaptive. Thus, the knee joint rotation is automatically controlled at substantially all speeds and for substantially all patients, regardless of body size, without pre-programmed information or calibrated data from a patient or prosthetist.

One main advantage of the preferred embodiments of the knee system is that it is able to adapt to various types of disturbances once the patient leaves the prosthetist's facility because it is patient-adaptive and speed-adaptive. As an example, when the patient picks up a suitcase, the knee responds to the disturbance automatically. With conventional technology, the patient would have to go back to the prosthetist facility to re-program their knee. In the preferred embodiments, the trial period is not typically "lengthy" and "fatiguing".

The prosthetic knee 110 of the preferred embodiments advantageously permits the amputee to move and/or adapt comfortably and safely in a wide variety of circumstances. For example, during walking, running, sitting down, or when encountering subtle or drastic changes in the environment or ambient conditions, such as, when the user lifts a suitcase or walks down a slope.

The artificial knee 110 provides stance control to limit buckling when weight is applied to the limb. In addition, the prosthetic knee 110 provides aerial swing control so that the knee reaches full extension just prior to or at heel-strike in a smooth and natural manner.

Preferably, the artificial knee system 110 of the present invention is used in conjunction with a trans-femoral (above-knee, A/N) amputee. Alternatively or optionally, the prosthetic knee 110 may be adapted for use with a knee-disarticulation (K/D) amputee where the amputation is through the knee joint, as needed or desired, giving due consideration to the goals of achieving one or more of the benefits and advantages as taught or suggested herein.

Knee Electronics

Figure 5B:
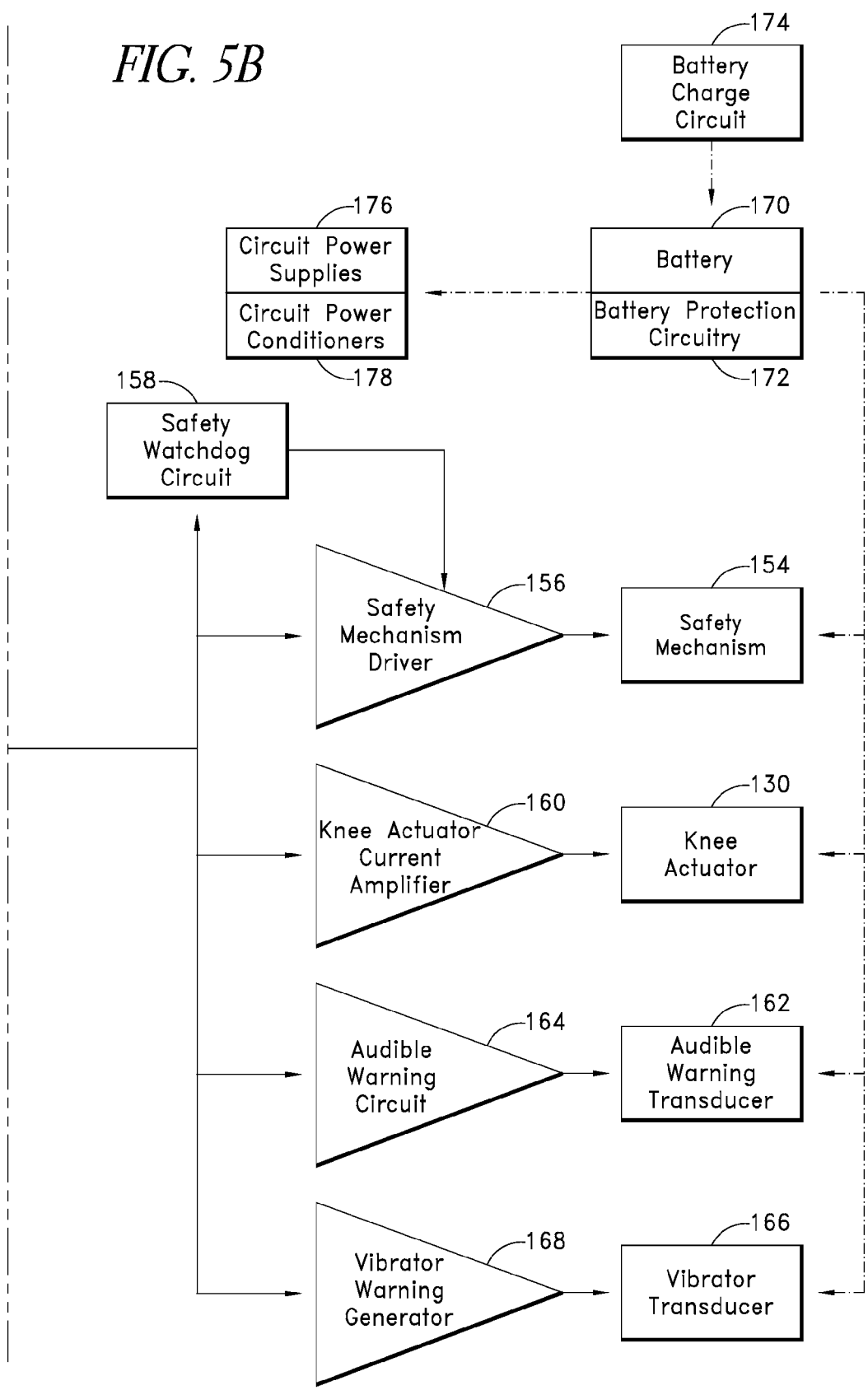
FIG. 5 is a simplified block diagram representation of an adaptive prosthetic knee system having features and advantages in accordance with one preferred embodiment of the present invention.

FIG. 5 illustrates one preferred embodiment of the prosthetic knee system 110 of the invention in block diagram format. In FIG. 5, the solid communication lines represent signal/data flow and the phantom or dashed communication lines represent energy flow.

As stated above, preferably, the automated prosthetic knee system 110 generally comprises a variable-torque braking system or damper 130 and an onboard control unit or system 120. The feedback control system 120 comprises a central controller 132 which receives sensory and diagnostic information to control the operation of the knee actuator 130 and other associated equipment (as discussed below). For purposes of clarity, the various components of the prosthetic knee system 110, in accordance with one preferred embodiment, are listed in Table 2 below.

TABLE 2

| Component(s) | Reference Numeral |
| --- | --- |
| Knee Actuator | 130 |
| Microprocessor | 132 |
| Knee Angle Sensor | 134 |
| Knee Angle Amplifier | 136 |
| Knee Angle Differentiator | 138 |
| Axial Force and Moment Sensors | 140 |
| Axial Force and Moment Amplifiers | 142 |
| Battery Monitoring Circuit | 144 |
| Moisture Detection Circuit | 146 |
| Power-Usage Monitoring Circuit | 148 |
| Memory | 150 |
| Serial Communications Port | 152 |
| Safety Mechanism | 154 |
| Safety Mechanism Driver | 156 |
| Safety Watchdog Circuit | 158 |
| Knee Actuator Current Amplifier | 160 |
| Audible Warning Transducer | 162 |
| Audible Warning Circuit | 164 |
| Vibration Transducer | 166 |
| Vibration Warning Generator | 168 |
| Battery | 170 |
| Battery Protection Circuitry | 172 |
| Battery Charge Circuit | 174 |
| Circuit Power Supplies | 176 |
| Circuit Power Conditioners | 178 |

As mentioned above, the knee actuator 130 comprises a variable torque brake or damper for modulating joint damping to control extension and flexion movements based on command signals from the knee controller 132. The manner in which the control scheme of the preferred embodiments controls knee joint rotation is discussed in further detail later herein.

The knee actuator or brake 130 can comprise any one of a number of conventional brakes. These include without limitation (i) dry friction brakes where one material surface rubs against another surface with variable force; (ii) viscous torque brakes using hydraulic fluid squeezed through a variable sized orifice or flow restriction plate; and (iii) magnetorheological (MR) brakes or dampers where MR fluid (containing small iron particles suspended in the fluid) is squeezed through a fixed orifice or flow restriction plate, with viscosity of the fluid being varied in response to an applied magnetic field. Optionally, the knee brake 130 comprises a pneumatic brake, as known in the art.

In one preferred embodiment, and as discussed in further detail later herein, the knee brake 130 comprises a variable torque rotary magnetorheological (MR) brake that operates in the shear mode. MR fluid is sheared between a plurality of rotors and stators to generate a variable and controlled damping effect which precisely and accurately modulates the knee joint rotation.

In one preferred embodiment, the prosthetic knee system 110 comprises an artificial knee cap or extension stop to limit the maximum knee extension. The artificial or prosthetic knee cap is preferably below the knee actuator 130 and is mechanically connected to the knee actuator 130 and/or the frame 141.

The knee actuator current amplifier 160 comprises a circuit which generates the needed or desired current from the battery 170 in the knee actuator 130 to modulate the damping torque provided by the knee brake 130. Command signals or instructions from the microprocessor 132 to the knee actuator current amplifier 160 determine the current supplied to the knee actuator 130, and hence the amount of damping torque generated.

The onboard microprocessor 132 including memory 150 are local to the prosthetic knee system 110. The microprocessor 132 is the primary computational unit of the prosthetic knee system 110 and receives input electrical signals from the various components of the knee system 110, processes them, and generates output electrical signals to monitor and control the actuations of the prosthetic knee 130 and other associated components, as necessary.

The microprocessor 132 includes circuitry which digitizes incoming signals and generates outgoing analog signals. The microprocessor further includes timing modules and watchdog self-resetting circuitry. The memory 150 comprises internal or external volatile and non-volatile memory.

The microprocessor 132 preferably comprises a Motorola 68HC12B32 16 bit series microprocessor. This processor has 8 channel analog to digital conversion capability, 32K of flash and 768 bytes of EEProm memory. The external memory comprises two industry standard 32K by 8 bit static RAMs. The serial flash is an Atmel AT45D081 and uses the serial communications interface (SCI) provided by the microprocessor.

The serial communications port 152 provides an interface between the knee electronics, via the microprocessor 132, and external diagnostic, data logging and programming equipment. The port 152 can efficaciously comprise any one of a number of commercially available communication ports, for example, RS232, RS485, ethernet and the like, as needed or desired, giving due consideration to the goals of achieving one or more of the benefits and advantages as taught or suggested herein.

The microprocessor 132 along with the other associated sensory, diagnostic safety and protection circuitry of the prosthetic knee system 110 are preferably mounted on a circuit board to provide a compact assembly. The circuit board is preferably housed within and secured to the frame 141 directly or utilizing an intermediate shell or cover to protect the circuit board and components mounted thereon.

The knee angle sensor 134 is used to encode the absolute knee angle. Preferably, the knee angle sensor 134 measures the degree to which a single degree-of-freedom knee joint is flexed or extended. The knee angle amplifier 136 comprises a circuit which conditions the signal received from the knee angle sensor 134 and feeds it to the microprocessor 132 for knee control purposes, as discussed below.

The knee angle differentiator 138 comprises a circuit which differentiates the signal received from the knee angle sensor 134 to determine the rotational or angular velocity of the knee and feeds this signal to the microprocessor 132 for knee control purposes, as discussed below. The knee angular velocity signal further determines whether the knee is flexing or extending.

The angle sensor 134 is preferably mounted on the frame 141 (FIG. 4). Alternatively, the angle sensor 134 is mounted on the side of the knee actuator 130 or directly below the knee actuator 130, as needed or desired.

In one preferred embodiment, the angle sensor 134 comprises an angle sensing potentiometer. In another preferred embodiment, the angle sensor 134 comprises an optical shaft encoder. In yet another preferred embodiment, the angle sensor 134 comprises a magnetic shaft encoder. In other preferred embodiments, alternate knee angle sensing devices may be utilized with efficacy, as required or desired, giving due consideration to the goals of accurately estimating the knee angle, and/or of achieving one or more of the benefits and advantages as taught or suggested herein.

The axial force and moment sensors 140 comprise a transducer that generates signals proportional to the lower leg axial force and moment or torque. In one preferred embodiment, the transducer comprises a fore strain gage sensor and an aft strain gage sensor. To compute axial force, the fore and aft signals are added, and to compute the moment, the signals are subtracted. The axial force and moment amplifiers 142 condition the signals received from the axial force and moment sensors 140 and feed it to the microprocessor 132 for knee control purposes, as discussed below.

The axial force sensors 140 measure the component of force applied to the knee prosthesis 110 from the ground or other supporting surface in a direction substantially along or parallel to the shin longitudinal axis 180 (FIG. 4) or knee long axis. The axial force measurement is used to determine whether the prosthetic foot 108 (FIG. 4) is on or off the ground or other supporting surface. That is, a zero axial force indicates that the foot 108 is not on the ground, for example, in the swing phase, while a non-zero axial force indicates that the foot 108 is on the ground, for example, in the stance phase.

The torque or moment sensors 140 measure the component of torque applied to the knee prosthesis 110 in a medial-lateral direction 182 as shown in FIG. 4. In addition, the moment sensors 140 determine whether the applied knee moment is a flexion or extension moment. Typically, at heel strike a flexion moment is applied to the knee prosthesis 110, tending to flex the knee joint, and throughout late stance an extension moment is applied, tending to extend the joint.

The axial force and moment sensors 140 are preferably mounted on the frame 141 (FIG. 4). In one preferred embodiment, the axial force and moment sensors 140 comprises a strain gauge load cell. In another preferred embodiment, the axial force and moment sensors 140 comprise a deflection encoded shock/spring mechanism. In other preferred embodiments alternate load and/or moment sensing devices may be utilized with efficacy, as required or desired, giving due consideration to the goals of accurately estimating the axial load and/or applied moment, and/or of achieving one or more of the benefits and advantages as taught or suggested herein.

In one preferred embodiment, the axial force and moment sensors 140 comprise a plurality of strain gauges. Preferably, four gauges are used with two strain gauges mounted on the front 184 of the frame 141 and two strain gauges mounted on the rear 186 of the frame 141 to measure and differentiate between load on the heel of the foot 108 and load on the toe of the foot 108. Stated otherwise, the strain measurement provides an indication as to whether the center of gravity is in an anterior, centered or posterior position relative to the prosthetic foot 108.

The strain gauges are preferably arranged in a wheatstone bridge configuration to generate an electric signal which changes proportionally with bending moment strain. As the skilled artisan will recognize, such a wheatstone bridge configuration is a standard arrangement for determining the resistance change of strain gauges.

The battery monitoring circuit 144 continuously or periodically monitors the battery voltage, current and temperature for safety purposes. The data from the battery monitoring circuit 144 is continuously or periodically provided to the microprocessor 132 to facilitate in constraining the knee operation to within the battery manufacturer's specification.

The moisture detection circuit 146 continuously or periodically monitors the moisture levels for safety purposes and senses any abnormal moisture on the system circuit board and/or other associated system circuitry due to condensation, submersion and the like. The data from the moisture detection circuit 146 is continuously or periodically provided to the microprocessor 132.

In one preferred embodiment, the moisture detection circuit 146 comprises interdigitated copper traces. In other preferred embodiments, the moisture detection circuit can comprise alternate moisture detecting devices with efficacy, as required or desired, giving due consideration to the goals of reliably detecting moisture levels on the system electronics, and/or of achieving one or more of the benefits and advantages as taught or suggested herein.

The power usage monitoring circuit 148 continuously or periodically measures the power consumption by the knee actuator 130 for safety purposes. The data from the power usage monitoring circuit 148 is continuously or periodically provided to the microprocessor. In addition, the power usage monitoring circuit 148 or other independent circuits may be utilized, as needed or desired, to measure the power consumption by other electronic components of the prosthetic knee system 110.

The prosthetic knee system 110 preferably comprises a safety system including the safety mechanism 154. The safety mechanism 154 is actuated or activated to put the system 110 in a default safety mode when a system error is detected by the microprocessor 132. Such a system error can occur if abnormal behavior is noted in any of the signals from the knee angle sensors 134, the axial force and moment sensors 140, the battery monitoring circuit 144, the moisture detection circuit 146 and the power usage monitoring circuit 148 indicating a system malfunction and/or other concern over the integrity of the knee actuator 130.

Detection of a system error causes the safety mechanism or actuator 154 to activate a safety default mode such that even with a system malfunction the prosthetic knee system 110 remains safe for the amputee. For example, in the safety default mode, the knee could resist flexion but could be free to extend, thereby ensuring the safety of the patient.

The safety mechanism driver 156 comprises a power amplifier that turns on or off the safety default mode of the safety mechanism 154 based on command signals or instructions from the microprocessor 132. The safety watchdog circuit 158 comprises a circuit which is periodically or continuously "attended" to by signals from the microprocessor 132 to prevent the watchdog circuit 158 from unnecessarily enabling the safety default mode by sending signals to the safety mechanism driver 156. In other words, the safety watchdog circuit 158 would activate the safety mechanism 154 unless otherwise periodically or continuously instructed so by the microprocessor.

Preferably, and when possible, to warn the user of a system malfunction or unusual operating condition, prior to the activation of the default safety mode, either one or both of the audible warning transducer 162 and the vibration transducer 166 are activated. The audible warning circuit 164 comprises an amplifier which generates an electronic signal to create audible noise by the warning transducer 162 when enabled. The audible warning circuit 164 receives command signals or instructions from the microprocessor 132.

The audible warning transducer 162 is preferably housed in or secured to the frame 141 (FIG. 4). In one preferred embodiment, the audible warning transducer 162 comprises a piezo speaker. In other preferred embodiments, alternate sound generating devices may be utilized with efficacy, as required or desired, giving due consideration to the goals of warning the user, and/or of achieving one or more of the benefits and advantages as taught or suggested herein.

The vibration transducer 166 comprises an actuator which vibrates the prosthetic knee system 110 in such a way as to draw attention from the wearer. The vibration warning generator 168 comprises an amplifier which generates an electronic signal to turn on the vibration transducer 164 when enabled. The vibration warning generator 168 receives command signals or instructions from the microprocessor 132.

The vibration transducer 166 is preferably mounted on the system circuit board. Alternatively, the vibration transducer 166 is housed in or secured to the frame 141 (FIG. 4). In one preferred embodiment, the vibration transducer 166 comprises a wobble motor. In other preferred embodiments, alternate vibration generating devices may be utilized with efficacy, as required or desired, giving due consideration to the goals of warning the user, and/or of achieving one or more of the benefits and advantages as taught or suggested herein.

The onboard battery or power source 170 supplies power to the knee actuator 130, the safety mechanism 154, the audible warning transducer 162 and the vibration transducer 166. The circuit power conditioners 178 convert the raw battery power to power that is conditioned for use by the microprocessor 132 and other sensory circuitry and individual system subcircuits. The circuit power supplies 176 provide the conditioned power to the microprocessor 132 and other sensory circuitry and individual system subcircuits.

Thus, via the circuit power supplies 176 and the circuit power conditioners 178, the battery 170 distributes power to the microprocessor 132 and other sensory circuitry and individual system subcircuits including the knee angle amplifier 136, the knee angle differentiator 138, the axial force and moment amplifiers 142, the battery monitoring circuit 144, the moisture detection circuit 146, the power usage monitoring circuit 148, the safety watchdog circuit 158, the safety mechanism driver 156, the knee actuator current amplifier 160, the audible warning circuit 164, the vibrator warning generator 168 and any other associated circuits, as necessary.

The battery protection circuitry 172 protects the battery 170 from exceeding safe operating conditions. If desired, a battery state of charge indicator may also be provided. The battery charge circuitry 174 converts power from a charging source, typically a wall outlet, to the power levels suited for the battery 170.

The Control Scheme

The State Machine

Figure 6:
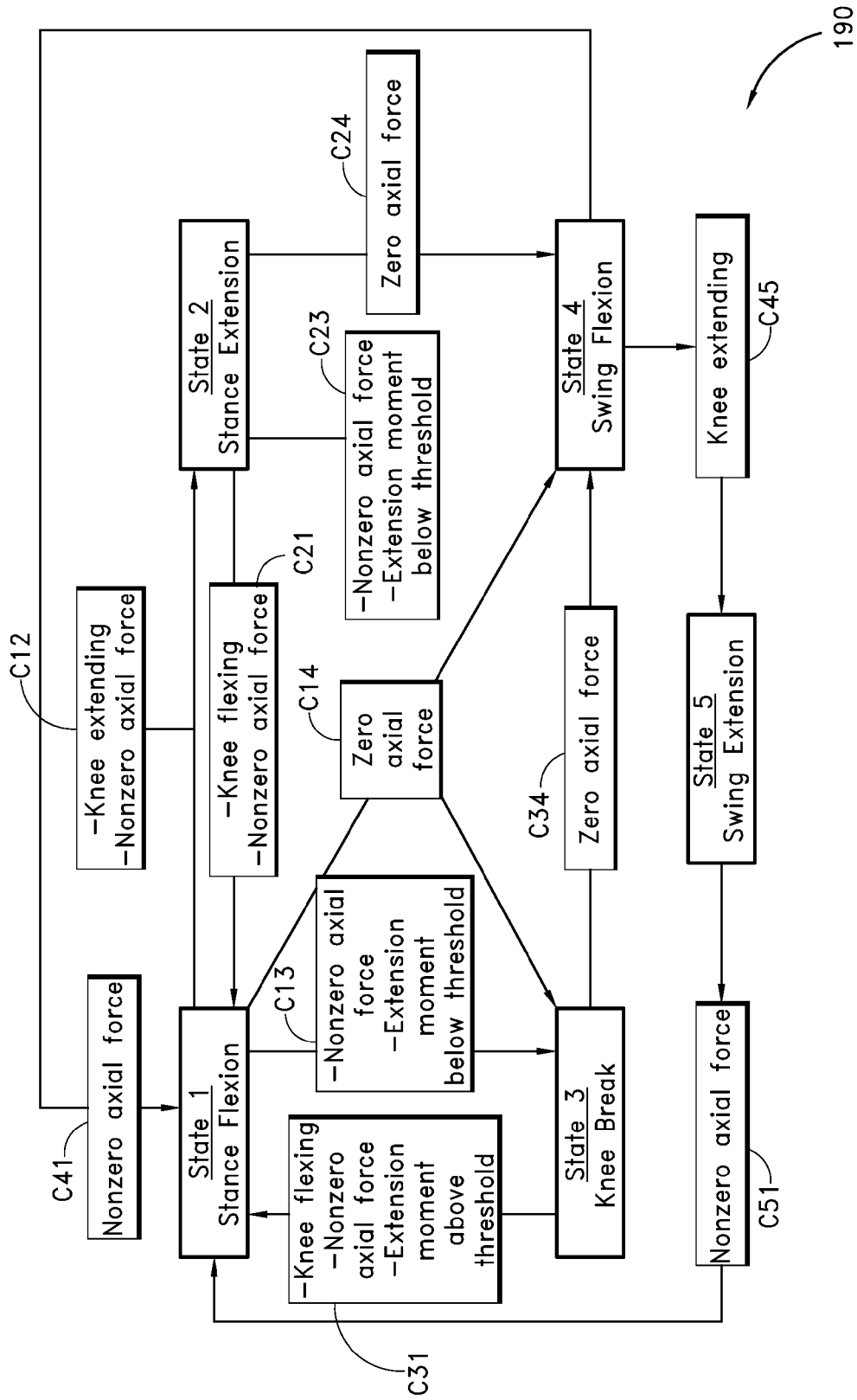
FIG. 6 is a diagram of one preferred embodiment of a state machine controller for the prosthetic knee system of FIG. 5 and showing state-to-state transitional conditions for a gait or activity cycle.

The basic phases or states of biological gait (as discussed above) suggest the framework of the prosthetic knee controller as a state machine. Thus, each phase corresponds to a State 1 to 5 (see, for example, FIG. 2 and Table 1). FIG. 6 is a diagram of one preferred embodiment of a state machine controller 190 of the prosthetic knee system 110 and shows state-to-state transitional conditions.

As discussed above, the onboard knee angle sensor 134 measures the knee angle and the onboard axial force and moment sensors 140 measure the axial force and the knee moment. The knee angle data, the knee rotational velocity data, the axial force data and the knee moment data are provided to the microprocessor or main controller 132 to determine system state, and accordingly automatically control the actuations of the knee brake or actuator 130 to modulate knee joint rotation.

Also as discussed above, the knee angle signal determines the degree of knee joint rotation and the knee angular velocity signal determines whether the knee is flexing or extending. The axial force measurement determines whether the prosthetic foot is on or off the ground or other supporting surface. The knee moment measurement determines whether the applied knee moment is a flexion or extension moment.

Based upon these sensory data provided to the microprocessor 132, the state machine controller 190 cycles through the various States 1, 2, 3, 4 and 5 as the user moves through each gait cycle or other locomotory activity. Often, and as seen in FIG. 6, the controller 190 changes state depending on whether the moment is above or below an extension moment threshold or critical value. Advantageously, and as discussed below, these threshold moments are automatically self-learned or self-taught by the prosthetic knee system of the preferred embodiments for each individual patient without pre-programmed information about the specific patient.

Preferably, the control of the state machine 190 on the behavior of the knee damper 130 allows the patient to perform a wide variety of activities. These include normal walking or running on a level or inclined surface, sitting down, ascending or descending steps or other situations, for example, when a user lifts a suitcase. Again, in these and other situations, the prosthetic knee system of the preferred embodiments automatically provides for accurate knee damping control without pre-programmed information about the specific patient.

The overall operation of the state machine controller 190 and the various conditions that are satisfied between state-to-state transitions are now described in accordance with one preferred embodiment. Based on the input sensory data (as described above) these provide information to the knee brake 130 on how to modulate knee damping. The control actions for each state are described later herein.

First, the state transitions and conditions for these transitions are described for a typical walking or running cycle. As stated above, the axial force is the component of force applied to the knee prosthesis 110 from the ground or other supporting surface in a direction substantially along or parallel to the shin longitudinal axis 180 (FIG. 4) or knee long axis. The applied moment is the component of torque applied to the knee prosthesis 110 in a medial-lateral direction 182 as shown in FIG. 4.

State 1 (stance flexion) transitions to State 2 (stance extension) under condition C12. Condition C12 is satisfied when the knee first achieves a small extension velocity. At this stage, the prosthetic foot is on the ground or other supporting surface.

State 2 (stance extension) transitions to State 3 (knee break) under conditions C23. Conditions C23 are satisfied when the extension moment is below a threshold or critical level or value, when the knee is at or close to full extension, and when the knee has been still for a certain amount of time.

State 3 (knee break) transitions to State 4 (swing flexion) under condition C34. Condition C34 is satisfied when the axial force falls below a threshold or critical level or value. That is, at this stage the prosthetic foot is off or nearly off the ground or other supporting surface.

State 4 (swing flexion) transitions to State 5 (swing extension) under condition C45. Condition C45 is satisfied when the knee first begins to extend. At this stage, the prosthetic foot is still off the ground or other supporting surface.

State 5 (swing extension) transitions back to State 1 (stance flexion) under condition C51. Condition C51 is satisfied when the axial force climbs above a threshold or critical level or value. This completes one walking or running gait cycle.

As indicated above, the state-to-state transitions may follow other patterns than the State 1 to State 2 to State 3 to State 4 to State 5 scheme depending on the particular activity of the amputee and/or the ambient or terrain conditions. Advantageously, the finite state machine controller 190 automatically adapts to or accommodates for situations in which alternate state transitions may occur to provide the amputee with options of achieving a wide variety of substantially life-like or natural movements under diverse external conditions.

State 1 (stance flexion) transitions to State 3 (knee break) under conditions C13. Conditions C13 are satisfied when the extension moment is below a threshold or critical level or value, when the knee is at or close to full extension, and when the knee has been still for a certain amount of time. This state transition from State 1 to State 3 can occur when the amputee fails to go through the normal flexion-extension cycle during stance.

State 1 (stance flexion) transitions to State 4 (swing flexion) under condition C14. Condition C14 is satisfied when the axial force falls below a small but nonzero threshold or critical level or value. This state transition from State 1 to State 4 can occur when the amputee stands on the knee but alternately shifts back and forth, weighting and unweighting the prosthesis.

State 2 (stance extension) transitions to State 1 (stance flexion) under condition C21. Condition C21 is satisfied when the knee achieves a small but nonzero flexion velocity. This state transition from State 2 to State 1 can occur if the amputee begins to flex the knee during the extension period of stance.

State 2 (stance extension) transitions to State 4 (swing flexion) under condition C24. Condition C14 is satisfied when the axial force falls below a threshold or critical level or value. This state transition from State 2 to State 4 can occur if the amputee lifts his foot during the extension period of stance.

State 3 (knee break) transitions to State 1 (stance flexion) under conditions C31. Conditions C31 are satisfied when the knee has been in State 3 for a certain amount of time, OR if the extension moment is above a threshold or critical level AND when the knee is at full extension or close to full extension. This state transition from State 3 to State 1 can occur if the amputee leans back on his heels from a standing position.

State 4 (swing flexion) transitions to State 1 (stance flexion) under condition C41. Condition C41 is satisfied when the axial force climbs above a small but nonzero threshold or critical value. This state transition from State 4 to State 1 can occur if the amputee stands on the knee but alternately shifts back and forth, weighting and unweighting his prosthesis.

As discussed above, based upon input sensory data, the controller 190 cycles through the states as the user moves through each gait cycle or activity. The state machine software is resident within the microprocessor 132 or memory 150. Next, the various control actions or scheme for each state are described. The control scheme for States 1, 2 and 3 is referred to as "stance phase control" and the control scheme for States 4 and 5 is referred to as "swing phase control."

Stance Phase Control

In accordance with one preferred embodiment, a scheme is provided to adaptively control the stance phase damping of a prosthetic knee worn by a patient. Stored in the memory of the prosthetic knee are correlations relating sensory data and stance phase damping. Established in clinical investigations of amputees of varying body size these relations characterize knee behavior when the prosthetic foot is in contact with the ground. Sensory information are used in conjunction with these correlations to define how stance phase damping should be modulated in standing, walking and running.

In accordance with one preferred embodiment, an adaptive prosthetic knee is provided for controlling the knee damping torque during stance phase of an amputee. The prosthetic knee generally comprises a controllable knee brake, sensors and a controller. The knee brake provides a variable damping torque in response to command signals. The sensors measure knee angle, axial force and applied moment as the amputee moves over a supporting surface. The controller has a memory and is adapted to communicate command signals to the knee brake and receive input signals from the sensors. The memory has stored therein relationships between sensory data and stance phase damping established in prior clinical investigations of patients of varying body size. In addition, biomechanical information is stored in memory to guide the modulation of damping profiles. The controller utilizes sensory data from the sensors in conjunction with both clinical and biomechanical information to adaptively and automatically control the damping torque provided by the knee brake during stance phase independent of any prior knowledge of patient size.

State 1 (Stance Flexion) and State 2 (Stance Extension):

In normal gait, the knee first flexes and then extends throughout early to midstance (see FIGS. 2 and 3). In State 1, or stance flexion, a prosthetic knee should preferably exert a resistive torque or damping to inhibit the knee from buckling under the user's weight. A prosthetic knee should also preferably exert a resistive torque or damping during the extension period of stance, or State 2, to slow or damp knee extension so that the knee does not overextend, thereby preventing the rotating portion of a knee, such as the knee brake, to slam against a prosthetic kneecap (extension stop) or outer knee cover.

The degree to which a prosthetic knee should dampen flexion and extension so as to closely simulate a life-like or natural response is largely dependent on body weight. That is, in States 1 and 2 larger damping values are preferred for larger users so as to more faithfully simulate a generally life-like or natural feel. (Note that in general a tall user does require a greater knee resistance but tall people typically tend to rotate the knee faster thereby increasing the torque response of the system—current is proportional to knee rotational velocity where the proportionality constant is knee damping.)

In accordance with one preferred embodiment, clinical studies were performed with amputees of different body sizes ranging from small/light to large/heavy to generally capture the full range of body sizes. These users utilized prosthetic knees and other sensory equipment. Preferably, the users utilized the prosthetic knee brake 130 along with the axial and moment sensors 140 and the knee angle sensor 134.

In these clinical investigations, flexion and extension damping values provided by the knee actuator 130 were optimized for amputees of different body size while monitoring the axial force, knee moment, knee angle and knee angular velocity data, among other associated data, as necessary. These data were then used to establish relationships or correlations between stance phase resistances and sensory information measured and/or computed during stance.

Preferably, the clinical study data is collected over a wide variety of patient activities and/or external conditions and terrain. These include normal walking or running on a level or inclined surface, sitting down, ascending or descending steps or other situations, for example, when a user lifts a suitcase, among other.

The optimized stance phase knee resistance or damping and sensory data relationships or correlations for patients of varying body size are stored or programmed in the controller or microprocessor 132 or system memory 150. These are used in the prosthetic knee system 110 of the preferred embodiments to automatically control the actuations of the knee brake 130.

When an amputee first walks utilizing the prosthetic knee system 110 as controlled by the preferred control schemes of the invention, preferably, the microprocessor or controller 132 initially sets State 1 damping or resistance to knee rotation to a large value. For a linear damper in which torque is proportional to knee rotational velocity, an adequate proportionality constant, or damping value, is 20 Nm*seconds per radian. This ensures that the prosthetic knee 110 is safe and does not buckle to exceedingly large flexion angles. Preferably, this maximum flexion angle does not exceed 15°.

In distinction to initial State 1 damping, preferably, the microprocessor or controller 132 initially sets State 2 damping or resistance to knee rotation to a smaller value. For a linear damper in which torque is proportional to knee rotational velocity, an adequate proportionality constant, or damping value, is 10 Nm*seconds per radian. This allows the amputee to extend the knee even if the knee happens to become flexed.

As the amputee starts moving and taking several steps, the axial force and moment sensors 140 and the angle sensor 134 are continuously or periodically providing axial force, applied moment, knee angle and knee angular velocity data or signals to the microprocessor or controller 132. These sensory data, and in particular the peak force and peak torque and/or the axial force and torque profiles applied to the prosthetic knee system 110, are used by the controller 132 to adjust the flexion and extension damping to values or profiles that were determined to give reasonable or optimized or generally life-like stance behavior during the prior clinical investigations.

As discussed above, the relationships or correlations obtained during these clinical investigations of a wide range of patients having varying body sizes have been programmed or stored in the controller 132. As the patient continues to use the prosthetic knee system 110, further automated refinements and fine-tuning can be made by the system 110, as necessary.

The prosthesis of the preferred embodiments is a self-teaching and/or self-learning system that is guided by clinical (prosthetic) and biomechanical knowledge. For example, biomechanical knowledge (stored in the system memory) includes information related to the mechanics of typical human walking/running, as discussed above in reference to FIG. 1.

Moreover, the clinical relationships or correlations also allow the prosthetic knee system 110 to determine the appropriate "threshold moments" for the particular amputee independent of body size. As discussed above, these threshold moments are used by the state machine 190 (FIG. 6) to change state depending on whether the threshold moment is above or below certain values specific to the patient.

Advantageously, in the preferred embodiments, no patient-specific information needs to be pre-programmed into the prosthetic knee by a prosthetist or the patient. Using sensory information measured local to the knee prosthesis, stance resistances automatically adapt to the needs of the amputee, thereby providing an automated patient-adaptive system.

State 3 (Knee Break):

In one preferred embodiment, State 3 (knee break) knee damping or resistance is maintained substantially constant and minimized so that the amputee can easily flex the knee. Preferably, this minimum value of the knee damping torque is about 0.4 N-m and is largely determined by the particular knee brake utilized. Alternatively, other minimum damping torque values and/or variable torques may be utilized with efficacy, as needed or desired, giving due consideration to the goals of achieving one or more of the benefits and advantages as taught or suggested herein.

In another preferred embodiment, the State 3 knee damping or torque is determined as described above for States 1 and 2. That is, measured sensory data, and in particular the peak force and peak torque and/or the axial force and torque profiles applied to the prosthetic knee system 110, are used by the controller 132 to adjust the knee resistance or damping to values or profiles that were determined to give reasonable or optimized or generally life-like stance behavior during prior clinical investigations.

Swing Phase Control

In accordance with one preferred embodiment, a scheme is provided of adaptively controlling the swing phase damping torque of a prosthetic knee worn by a patient as the patient travels at various locomotory speeds. The ground contact time of a prosthetic foot, measured from heel strike to toe-off, has been shown to correlate well with forward locomotory speed. The scheme comprises the step of continuously measuring foot contact time as an estimate of the patient's forward speed, and adaptively modulating swing phase damping profiles until the knee is comfortable and moves naturally. The swing phase damping profile for knee flexion is iteratively modulated to achieve a particular range of peak flexion angle. In distinction, for knee extension, knee damping is modulated to control the impact force of the extending leg against the artificial knee cap. The converged damping values are used to automatically control swing phase damping at all locomotory speeds.

In one preferred embodiment, during stance phase the controller 132 computes a parameter, based on input sensory data, that changes with locomotory speed of the amputee. Preferably, this parameter changes monotonically with locomotory speed. As discussed below, this parameter is used by the controller 132 to automatically control swing phase knee resistances for substantially all patients at substantially all speeds.

In one preferred embodiment, the speed control parameter is the amount of time the prosthetic foot remains in contact with the ground, or foot contact time. In another preferred embodiment, the speed control parameter is the maximum flexion velocity that occurs between substantially maximum or full extension and about thirty degrees flexion as the leg prosthesis flexes from State 3 to State 4. In other preferred embodiments, other suitable speed control parameters may be used, as needed or desired, giving due consideration to the goals of adaptively controlling knee resistances at various speeds, and/or of achieving one or more of the benefits and advantages as taught or suggested herein.

The foot contact time is preferably measured or computed during a particular time period. Preferably, the foot contact time is measured during one stance phase. Alternatively, the foot contact time may be measured or computed over one or more gait cycles. The foot contact time is preferably computed based on signals from the axial force sensors 140. A nonzero axial force measurement indicates that the prosthetic foot is in contact with the ground or other supporting surface.

Figure 7:
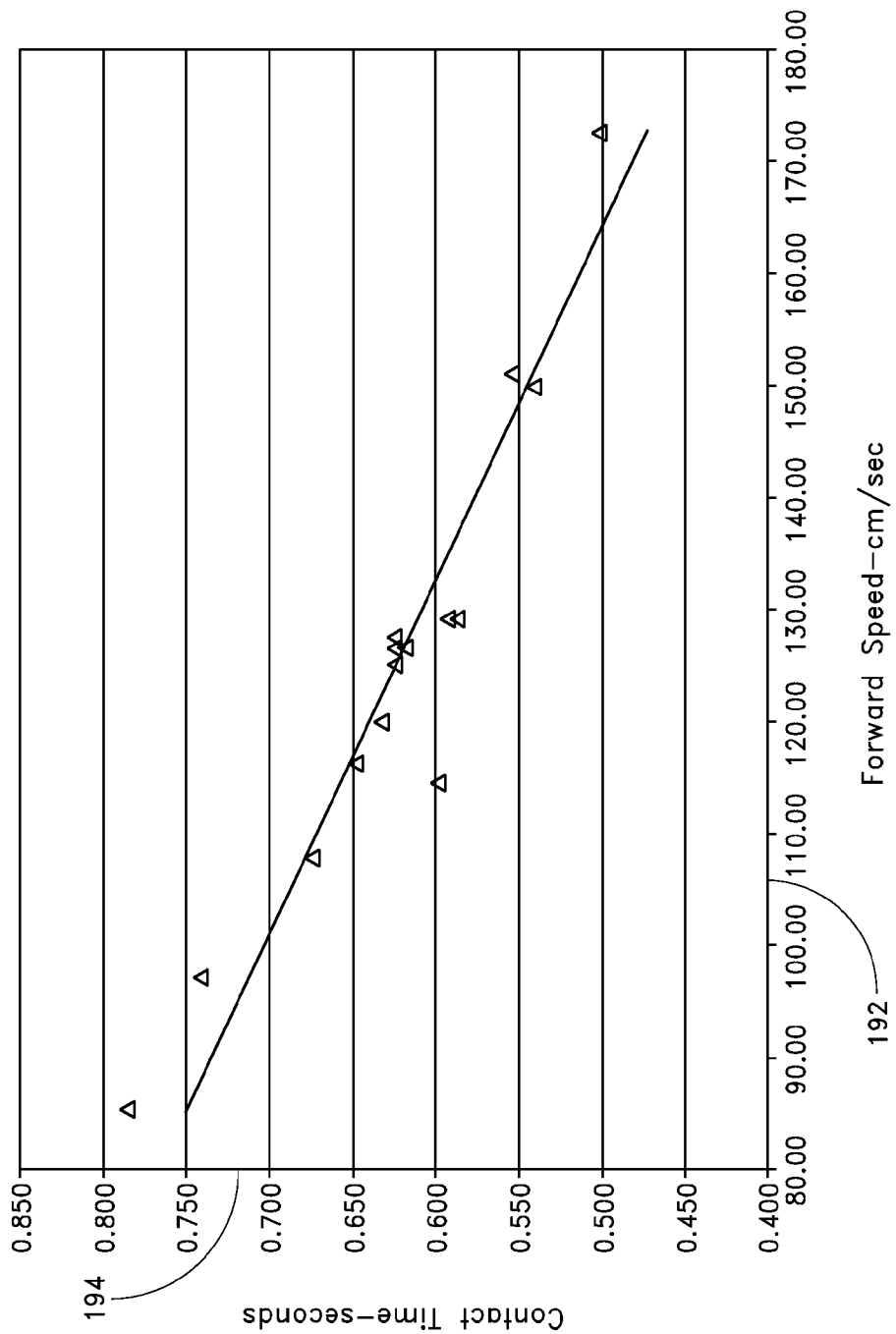
FIG. 7 is a graph of foot contact time plotted against forward speed for a non-amputee moving at several steady state speeds.

Referring to FIG. 7, typically, as walking speed increases, foot contact time decreases. In FIG. 7, foot contact time for one subject is plotted against forward walking and running speed, showing decreasing times with increasing speeds. The x-axis 192 represents the forward speed in cm/sec and the y-axis 194 represents the foot contact time during one stance phase in seconds.

In FIG. 7, triangles show contact times for a non-amputee moving at several distinct steady state speeds from slow walking at 0.85 meters/sec to moderate running at 1.74 meters/sec. As seen in FIG. 7, contact time generally decreases with increasing speed. A least-squares regression line is fitted to the data with a slope of about −0.32 $sec^2$/meter. Similar regressions were observed for both amputees and non-amputees. Data were collected using a four-camera bilateral kinematic data-acquisition system based on Selspot II cameras from Selective Electronics Co., Partille, Sweden (Unpublished data from Massachusetts General Hospital Gait Laboratory, Boston, Mass.).

In accordance with one preferred embodiment, the controller 132 through an iterative process determines how swing phase knee resistances or damping are modulated with foot contact time or locomotory speed. The full biological range of foot contact time is stored in the memory 150 of the knee's processor 132. Typically, a person of short stature has, on average, smaller foot contact times compared with a person of tall stature. The full biological range stored in the memory 150 preferably includes both these extremes.

In one preferred embodiment, the memory 150 stores a foot contact time of zero to about two seconds which is generally more than sufficient to cover the full biological range of foot contact times. In other preferred embodiments, the memory may store a smaller or larger range of foot contacts times with efficacy, as required or desired, giving due consideration to the goals of covering the full biological range of foot contact times, and/or of achieving one or more of the benefits and advantages as taught or suggested herein.

Preferably, the foot contact time range is partitioned into time slots or partitions within the microprocessor memory 150. When an amputee moves from a slow to a fast walk different time slots or locomotory velocity ranges are sampled. Since the entire biological range is partitioned, each amputee, independent of height, weight or body size, samples multiple time slots when moving from a slow to a fast walk or run.

In one preferred embodiment, the partition size is about 100 milliseconds (msecs), thus giving a total of twenty time slots over a two-second foot contact time range or interval. Any one amputee would typically sample not all but a fraction of the twenty time slots when moving from a slow to a fast locomotory pace. In other preferred embodiments, the partition size can be alternately selected with efficacy, as required or desired, giving due consideration to the goals of achieving one or more of the benefits and advantages as taught or suggested herein.

The control scheme of one preferred embodiment preferably modulates knee damping profiles within each time slot. In State 4, damping values are modulated within each time slot to control peak flexion angle, and in State 5, the impact force of the extending leg against the artificial knee cap is controlled. Based on sensory data provided to the controller 132 (as discussed above), the controller 132 sends appropriate command signals or instructions to the knee brake or damper 130.

State 4 (Swing Flexion):

When an amputee first walks or takes a first step utilizing the prosthetic knee system 110 as controlled by the preferred control schemes of the invention, preferably, the microprocessor or controller 132 initially sets or adjusts State 4 damping or resistance to knee rotation to its lowest value within each time slot. Hence, when an amputee takes a first step, State 4 knee damping torque is minimized, and the knee swings freely throughout early swing phase.

Preferably, this minimum value of the knee damping torque is about 0.4 N-m and is largely determined by the particular knee brake utilized. Alternatively, other minimum damping torque values and/or variable torques may be utilized with efficacy, as needed or desired, giving due consideration to the goals of achieving one or more of the benefits and advantages as taught or suggested herein.

For subsequent steps or gait cycles, after the first step, the controller 132 preferably increases brake damping by sending appropriate command signals or instructions to the knee brake 130 whenever the knee flexes to an angle greater than a fixed or predetermined target angle. For walking non-amputees, peak flexion angle during early swing typically does not exceed about 80° (see FIG. 3).

Hence, in accordance with one preferred embodiment, to achieve a gait cycle that is substantially natural or biological, the target angle is set equal to about 80° to control the State 4 peak flexion angle of the prosthetic knee system 110. In other preferred embodiments, and/or other activity levels or external conditions, the State 4 target angle can be alternately selected, as needed or desired, giving due consideration to the goals of providing a substantially life-like response, and/or of achieving one or more of the benefits and advantages as taught or suggested herein.

The microprocessor 132 preferably increases damping by an amount that is proportional to the error or difference between the actual flexion angle, measured by the angle sensor 134, and the target angle. Increased damping lowers the peak flexion angle for future gait cycles, but preferably only in those time slots or locomotory speeds which the amputee has sampled.

In State 4, when the peak flexion angle falls below the target angle the microprocessor 132 decreases the damping torque by sending appropriate command signals or instructions to the knee brake 130. This ensures that damping levels are not unnecessarily high.

Preferably, the damping torque is decreased when the peak flexion angle falls below the target angle for N consecutive locomotory steps, cycles or strides. One preferred value for N is about twenty locomotory or gait cycles, though other values may be efficaciously utilized. The brake damping is preferably decreased by an amount proportional to the error or difference between the actual flexion angle, measured by the angle sensor 134, and the target angle. Within any particular time slot or bin, decreased damping raises the peak flexion angle for future gait cycles.

Typically, at faster walking speeds, a greater damping level is required to keep the peak flexion angle in State 4 below the target angle threshold. Hence, to increase State 4 adaptation speed, in one preferred embodiment, the control scheme is designed such that damping levels at faster walking speeds or time slots are at least as high as damping levels at slower speeds or time slots.

Moreover, preferably, the State 4 damping levels applied in each time slot over one gait or locomotory cycle are constant, though they may be variable or angle dependent. Additionally, the modulation of State 4 damping levels in one or more time slots may involve changing the damping over a fixed or predetermined knee angle range or changing the angle range over which damping is applied or a combination thereof.

As the amputee continues to use the prosthetic knee system 110 and samples a diverse range of walking, running or other locomotory speeds, State 4 knee damping gradually converges within each time slot until peak knee flexion always falls below, or close to, the target angle for substantially all walking, running or other locomotory speeds. The optimized damping torque values or profiles for each time slot or locomotory speed are stored in the microprocessor memory 150. Hence, once the iterative adaptive control scheme has been implemented, the amputee can rapidly accelerate from a slow to a fast walk all the while sampling different time slots, and therefore, different damping levels within State 4.

State 5 (Swing Extension):

A similar scheme or strategy is used to control the force of impact when the swinging prosthesis strikes the artificial knee cap. As noted above, this artificial knee cap serves as an extension stop.

When an amputee first walks or takes a first step utilizing the prosthetic knee system 110 as controlled by the preferred control schemes of the invention, preferably, the microprocessor or controller 132 initially sets or adjusts State 5 damping to its lowest value within each time slot. Hence, when an amputee takes a first step, State 5 knee damping torque is minimized, and the knee extends from the peak flexion angle in State 4 to the maximum extension angle (about 180°) in State 5. Contact with the artificial knee cap prevents further extension.

Preferably, this minimum value of the knee damping torque is about 0.4 N-m and is largely determined by the particular knee brake utilized. Alternatively, other minimum damping torque values and/or variable torques may be utilized with efficacy, as needed or desired, giving due consideration to the goals of achieving one or more of the benefits and advantages as taught or suggested herein.

For subsequent steps or gait cycles, after the first step, the controller 132 computes an average impact force of the swinging leg against the artificial kneecap, within each bin or time slot, with the damping minimized. From the smallest of the M time slots or bins to the largest, if two consecutive bins are not directly adjacent then a linear extrapolation is performed to estimate the average impact forces for intermediate bins. For example, if averages are computed for bins "ten" and "twelve", but not for bin "eleven", then a linear extrapolation from the impact force corresponding to bin "ten" to the impact force corresponding to bin "twelve" is computed. This linear function is then employed to estimate an impact force for bin "eleven". The M bin region preferably comprises between about three to five bins or time slots, though fewer or more may be efficaciously used, as needed or desired.

After M average impact forces are computed and linear extrapolations are formulated from the minimum to the maximum bins, knee damping values are selected using a clinically determined relationship relating impact force to optimal extension damping. Hence, the amputee feels damping tending to decelerate the extending leg but only for walking speeds corresponding to the M bin region. For bins above the maximum and below the minimum, the default minimum damping is used until additional data are collected and average impact forces are computed. For bins above and below the original M bin region, linear extrapolations are preformed to estimate average impact forces for intermediate bins. For example, if the maximum of the original M bins is equal to "fourteen", and an average impact force is computed for bin "seventeen", then impact forces are estimated for bins "fifteen" and "sixteen" using a linear function from the average impact force corresponding to bin "fourteen" and the average force corresponding to bin "seventeen". Once average impact forces are computed for bins above and below the region of the original M bins, knee damping values are selected using a clinically determined relationship relating impact force to optimal extension damping.

The clinically determined relationship relating impact force to optimal extension damping is preferably derived or determined by a clinical investigation utilizing patients moving at different walking, running and or other locomotory speeds. Preferably, the clinically determined relationship relating impact force to optimal extension damping is derived or determined by a clinical investigation utilizing patients having different body sizes (weights). This clinically determined relationship is preferably stored in the system memory 150.

For each time slot or bin, once an optimal extension damping value has been selected, the microprocessor 132 once again computes an average impact force, and this new average force is then used as a target. If a system disturbance occurs that significantly alters the magnitude of impact force within a particular bin, then extension damping is modulated until the impact force is once again equal to, or in the proximity of, the target impact force. For example, within a particular bin, if the average impact force after the damping is turned on is 100 Newtons, and a disturbance causes the swinging leg to impact the artificial kneecap with a force of 150 Newtons, then extension damping is increased for that bin until the impact force is once again equal to, or approximately close to, the original 100 Newtons. With this adaptive routine, the amputee can change from a lightweight shoe to a heavy shoe and still walk comfortably without having to return to their prosthetist for re-programming.

The average impact force of the swinging leg against the artificial kneecap is preferably computed by the controller 132 using signals or data provided by sensors local to the prosthesis. The impact force sensors preferably comprise the sensors 140 and include one or more strain gauges mounted on or mechanically connected to the frame 141, as discussed above. Based on the computed or determined impact force, the controller 132 provides appropriate command signals or instructions to the knee brake 130 to control the knee damping.

State 5 damping, in each time slot or locomotory speed, can be modulated by several methods in the preferred embodiments of the control scheme of the invention. For example, the modulation of State 5 damping levels in one or more time slots may involve changing the damping over a fixed or predetermined knee angle range or changing the angle range over which damping is applied or a combination thereof. Additionally, State 5 damping levels applied in one or more time slots over one gait or locomotory cycle may be constant, variable and/or angle dependent.

In accordance with one preferred embodiment, the control scheme modulates the knee damping in State 5 over or within a fixed or predetermined angle range. For example, knee damping torque is increased or decreased within a particular extension angle range such as in the range from about 130° to about 180° to increase or decrease the damping within that particular time slot.

In accordance with another preferred embodiment, the control scheme keeps the State 5 knee damping levels substantially constant and instead modulates the angle range over which knee damping is applied. For example, the knee damping is constant and maximized, and this damping is applied over an extension angle range of about 170° to about 180°. To increase State 5 damping, the starting extension angle for the initiation of knee damping could be changed from about 170° to about 160° to increase the State 5 damping for that particular time slot or locomotory speed.

Typically, at faster walking speeds, a greater damping level is required to keep the impact force against the artificial kneecap at an acceptable range. Hence, to increase State 5 adaptation speed, in one preferred embodiment, the control scheme is designed such that damping levels at faster walking speeds or time slots are at least as high as damping levels at slower speeds or time slots.

As the amputee continues to use the prosthetic knee system 110 and samples a diverse range of walking and running speeds, State 5 knee damping gradually converges within each time slot until the impact forces of the swinging leg against the artificial kneecap are held at an acceptable level for substantially all walking, running or other locomotory speeds. The optimized damping torque values or profiles for each time slot or locomotory speed are stored in the microprocessor memory 150. Hence, once the iterative adaptive control scheme has been implemented, the amputee can rapidly accelerate from a slow to a fast walk all the while sampling different time slots, and therefore, different damping levels within State 5.

As the patient further continues to use the prosthetic knee system 110, further automated refinements and fine-tuning can be made by the system 110, as necessary. The prosthesis of the preferred embodiments is a self-teaching and/or self-learning system that is guided by clinical (prosthetic) and biomechanical knowledge. For example, biomechanical knowledge (stored in the system memory) includes information related to the mechanics of typical human walking/running, as discussed above in reference to FIG. 1.

Advantageously, no patient-specific is needed by the control scheme and prosthetic knee system of the preferred embodiments, and hence no pre-programming by a prosthetist or amputee is needed to accommodate different locomotory speeds and different patients. The system is able to adapt to various types of disturbances once the patient leaves the prosthetist's facility because it is patient-adaptive and speed-adaptive. Desirably, this also saves on time and cost, and substantially eliminates or mitigates inconvenience, discomfort and fatigue for the patient during an otherwise lengthy adjustment or trial period.

The control scheme and prosthesis of the preferred embodiments allow the patient to perform a wide variety of activities. These include normal walking or running on a level or inclined surface, sitting down, ascending or descending steps or other situations, for example, when a user lifts a suitcase.

Magnetorheological Knee Brake

Preferred embodiments of a magnetorheological knee brake or actuator in accordance with the present invention are described in copending U.S. application Ser. No. 09/767,367, filed Jan. 22, 2001, entitled "ELECTRONICALLY CONTROLLED PROSTHETIC KNEE," the entire disclosure of which is hereby incorporated by reference herein. For purposes of clarity and brevity of disclosure, only a brief description of this magnetorheological knee brake or actuator is set forth below.

Figure 8:
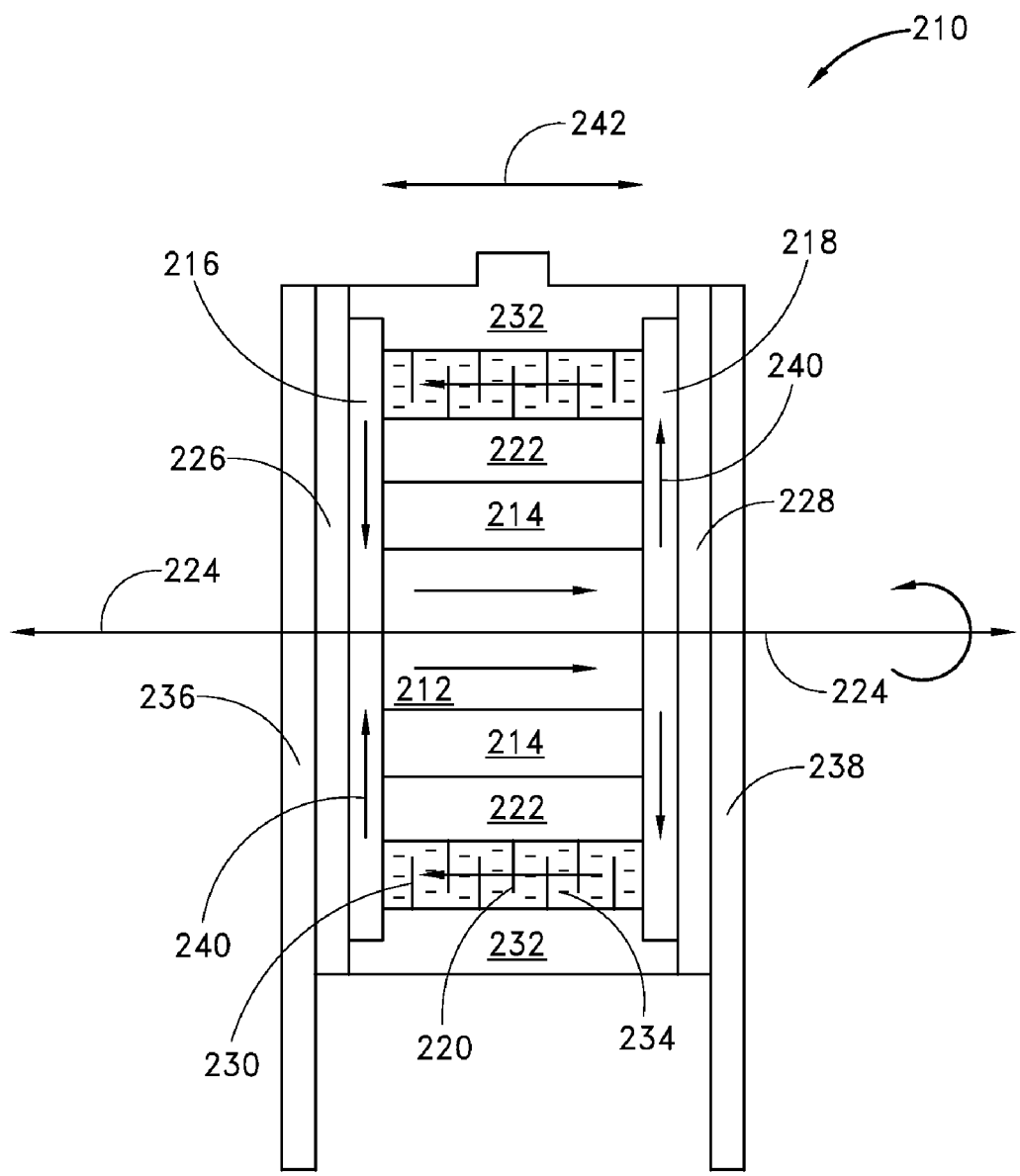
FIG. 8 is a simplified schematic drawing illustrating the general overall configuration of one preferred embodiment of the prosthetic knee actuator of the present invention.

FIG. 8 is a simplified schematic of a rotary prosthetic knee brake or magnetorheological (MR) braking system 210 in accordance with one preferred embodiment of the present invention. The knee actuator 210 includes a substantially central core 212 substantially circumscribed or enveloped by an electromagnet or magnetic coil 214 and in mechanical communication with a pair of side plates or disks 216, 218. By passing a variable, controlled current through the electromagnet 214, a variable magnetic field is created. Preferably, the core 212 and side plates 216, 218 are fabricated from a ferrous, magnetizable or magnetic material and the like. More preferably, the core 212 and side plates 216, 218 are fabricated from a magnetically soft material of high flux saturation density and high magnetic permeability.

The prosthetic knee brake or actuator 210 further includes a plurality of inner blades or plates 220 in mechanical communication with an inner spline 222. The inner spline 222 generally circumscribes or envelops the electromagnet 214 and is coupled or mechanically connected to the side plates 216, 218. The blades 220 are preferably concentrically arranged about the brake axis of rotation 224. The inner spline 222 is preferably rotatable about the knee joint axis of rotation 224, and hence so are the blades or rotors 220 and the core side plates 216, 218. Rotation of the inner spline 222 corresponds to rotation or movement of the lower (below the knee) part of the leg.

The prosthetic knee brake or actuator 210 also comprises a plurality of outer blades or plates 230 in mechanical communication with an outer spline 232. The outer spline 232 generally circumscribes or envelops the inner spline 222. The blades 230 are preferably concentrically arranged about the brake axis of rotation 224. The outer spline 232 is preferably rotatable about the knee joint axis of rotation 224, and hence so are the blades or stators 230. Rotation of the outer spline 232 corresponds to rotation or movement of the upper (above the knee) part of the leg. Preferably, the outer spline or housing 232 comprises means to facilitate connection of the prosthetic knee joint 210 to a suitable stump socket or the like. The outer spline 232, and hence the stators 230, are preferably substantially irrotationally coupled to or nonrotatable with respect to the stump socket or residual limb.

The plurality of rotors 220 and stators 230 are interspersed in an alternating fashion and the gaps between adjacent blades 220 and 230 comprise a magnetorheological (MR) fluid 234, which thereby resides in the cavity or passage formed between the inner spline 222 and the outer spline 232. In one preferred embodiment, the MR fluid 234 in the gaps or microgaps between adjacent rotors 220 and stators 230 is in the form of thin lubricating films between adjacent rotors 220 and stators 230. Shearing of MR fluid present between the side plates 216, 218 and adjacent stators 230 can also contribute to the knee damping.

During knee joint rotation, the MR fluid in the plurality of gaps between the rotors 220 and stators 230 is sheared to generate a damping torque to control the limb rotation. The blades or disks 220 and 230 are preferably formed of a ferrous, magnetizable or magnetic material and the like. More preferably, the blades or disks 220 and 230 are formed of a material of as high magnetic permeability and magnetic softness as is mechanically practical.

The knee joint actuator 210 further includes a pair of ball bearings 226, 228 coupled or connected to the respective side plates 216, 218. The ball bearings 226, 228 are further coupled or connected to respective side walls or mounting forks 236, 238. Thus, a rotary coupling is created between the inner spline 222 and the mounting forks 236, 238. The mounting forks 236, 238 in combination with the outer spline 232 form one main outer shell of the knee actuator 210. Preferably, the side walls or mounting forks 236, 238 comprise means to facilitate connection of the prosthetic knee actuator 210 to a suitable pylon, shank portion or the like.

Preferably, the central core 212 and the electromagnet 214 also rotate along with the rotation of the inner spline 222, the rotors 220, the core side plates 216, 218 and the mounting forks 236, 238. The stators 230 rotate together with the rotation of the outer spline 232.

The rotors 220 are rotationally fixed relative to the inner spline 222 and the stators 230 are rotationally fixed relative to the outer spline 232. During various stages of locomotion or knee rotation, and about the knee axis of rotation 224, the rotors 220 may rotate while the stators 230 are rotationally substantially stationary, or the stators 230 may rotate while the rotors 220 are rotationally substantially stationary, or both the rotors 220 and the stators 230 may rotate or be substantially rotationally stationary. The terms "rotor" and "stator" are used to distinguish the inner blades 220 and the outer blades 230, though both rotors 220 and stators 230 can rotate, and teach that relative rotational motion is created between the rotors 220 and the stators 230 (with MR fluid being sheared in the gaps between adjacent rotors 220 and stators 230). If desired, the blades 220 can be referred to as the "inner rotors" and the blades 230 as the "outer rotors."

Actuation of the magnet 214 causes a magnetic field, circuit or path 240 to be generated or created within the knee actuator 210. In one preferred embodiment, the magnetic field 240 passes through the central core 212, radially outwards through the side plate 218, laterally through the interspersed set of rotors 220 and stators 230 and the magnetorheological fluid 234, and radially inwards through the side plate 216. The portion of the magnetic field 240 passing through the core 212 and side plates 216, 218 generally defines the magnetic return path while the active or functional magnetic field is generally defined by the magnetic path through the rotors 220, stators 230 and MR fluid 234.

The magnetorheological (MR) fluid 234 undergoes a rheology or viscosity change which is dependent on the magnitude of the applied magnetic field. In turn, this variation in fluid viscosity determines the magnitude of the shearing force/stress, torque or torsional resistance generated, and hence the level of damping provided by the prosthetic knee brake 210. Thus, by controlling the magnitude of this magnetic field, the rotary motion of the artificial limb is controlled, for example, to control the flexion and extension during swing and stance phases to provide a more natural and safe ambulation for the amputee.

In one preferred embodiment, the rotors 220 and/or stators 230 are displaceable in the lateral direction 242, and hence under the influence of a magnetic field can rub against adjacent rotors 220 and/or stators 230 with a variable force determined by the strength of the magnetic field to create a "hybrid" magnetorheological and frictional damping brake. In another preferred embodiment, the rotors 220 and stators 230 are laterally fixed in position relative to the splines 222 and 232, and hence the braking effect is substantially purely magnetorheological or viscous. Alternatively, some of the rotors 220 and/or stators 230 may be laterally fixed while others may be laterally displaceable, as required or desired, giving due consideration to the goals of providing a substantially natural feeling and/or safe prosthetic device, and/or of achieving one or more of the benefits and advantages as taught or suggested herein. In one embodiment, the side plates 216, 218 are laterally displaceable and contribute to the frictional damping due to frictional contact with adjacent stators 230.

Advantageously, by operating in the shear mode, there is no or negligible pressure build-up within the MR actuated prosthetic knee of the present invention. This substantially eliminates or reduces the chances of fluid leakage and failure of the knee, and hence desirably adds to the safety of the device.

Also advantageously, the multiple shearing surfaces or flux interfaces, provided by the preferred embodiments of the present invention, behave like a torque multiplier and allow the viscous torque level to be stepped up to a desired maximum value without the use of an additional transmission or other auxiliary component. For example, if two flux interfaces can provide a maximum viscous torque of about 1 N/m, then forty flux interfaces will be able to provide a viscous damping torque of about 40 N/m. In contrast, if a 40:1 step-up transmission is used to increase the viscous torque, disadvantageously, not only is the system reflected inertia magnified by a factor of about 1600, but the system weight, size and complexity are undesirably increased.

The multiple shearing surfaces or interfaces of the prosthetic knee actuator of the preferred embodiments also advantageously allow for a wide dynamic torque range to be achieved which permits safe and/or more natural ambulation for the patient. Desirably, the MR actuated prosthetic knee of the preferred embodiments provides a rapid and precise response. Again, this permits the patient to move in a safe and/or more natural manner.

Figure 9:
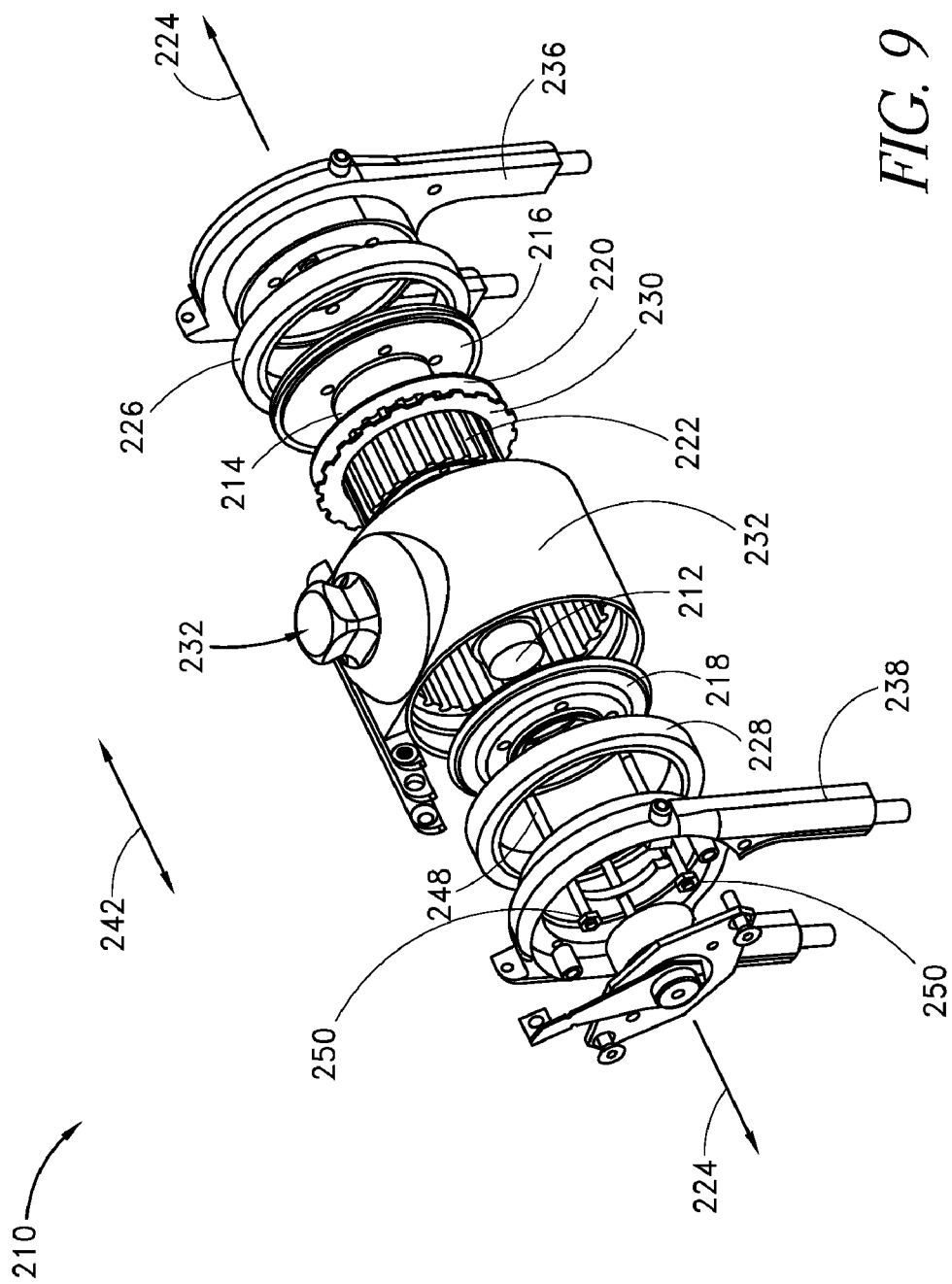
FIG. 9 is a detailed exploded perspective view of a magnetorheologically actuated prosthetic knee brake having features and advantages in accordance with one preferred embodiment of the present invention.
Figure 10:
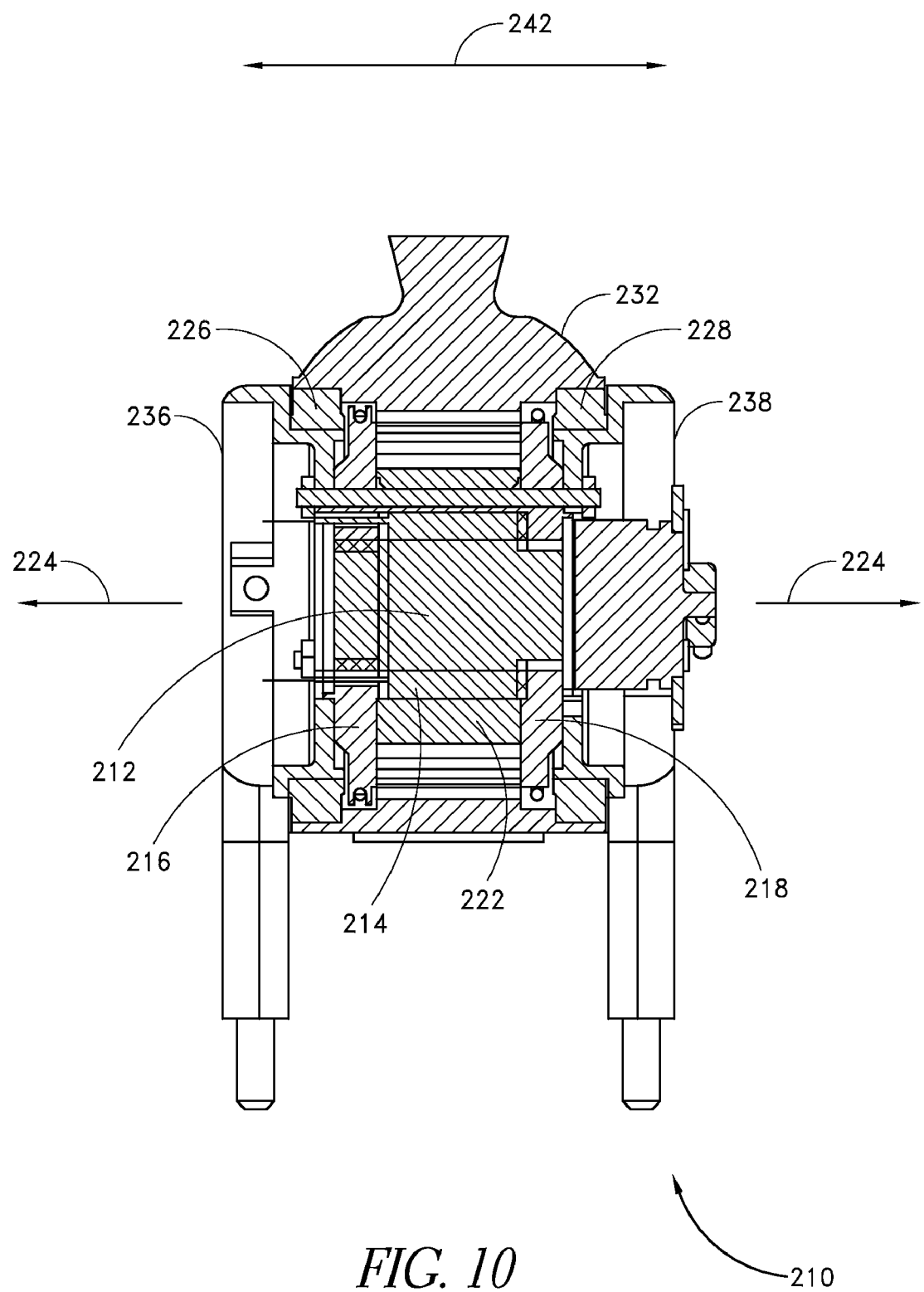
FIG. 10 is a cross section view of the prosthetic knee of FIG. 9.

FIGS. 9 and 10 show a magnetorheological rotary prosthetic knee actuator, brake or damper 210 having features and advantages in accordance with one preferred embodiment of the present invention. The prosthetic knee actuator 210 generates controllable dissipative forces preferably substantially along or about the knee axis of rotation 224. The knee actuator embodiment of FIGS. 9 and 10 is generally similar in operation and structure to the knee actuator embodiment of FIG. 8, and hence for purposes of clarity and brevity of disclosure only a brief description of the embodiment of FIGS. 9 and 10 is set forth below.

The electronically controlled knee actuator 210 generally comprises a generally central core 212 in mechanical communication with a pair of rotatable side plates 216, 218, an electromagnet 214, a plurality of blades or rotors 220 in mechanical communication with a rotatable inner spline 222, a plurality of blades or stators 230 in mechanical communication with a rotatable outer spline 232, a pair of ball bearings 226, 228 for transferring rotary motion to a pair of outer side walls or forks 236, 238. The rotation is substantially about the knee axis of rotation 224.

The plurality of rotors 220 and stators 230 are preferably interspersed in an alternating fashion and the gaps or microgaps between adjacent blades 220 and 230 comprise thin lubricating films of a magnetorheological (MR) fluid, which thereby resides in the cavity or passage formed between the inner spline 222 and the outer spline 232. This preferred embodiment provides a controllable and reliable artificial knee joint, which advantageously has a wide dynamic torque range, by shearing the MR fluid in the multiple gaps or flux interfaces between adjacent rotors 220 and stators 230.

Preferably, end-threaded rods 248 and nuts 250 are used to secure selected components of the prosthetic knee 210, thereby allowing a straightforward assembly and disassembly procedure with a minimum of fasteners. Alternatively, or in addition, various other types of fasteners, for example, screws, pins, locks, clamps and the like, may be efficaciously utilized, as required or desired, giving due consideration to the goals of providing secure attachment, and/or of achieving one or more of the benefits and advantages as taught or suggested herein.

In one preferred embodiment, the prosthetic knee brake 210 further comprises a flexion stop system or assembly. The flexion stop system controls the maximum allowable flexion angle by physically limiting the rotation between the outer side forks 236, 238 and the outer spline 232, and hence the rotation of the knee joint.

In one preferred embodiment, the prosthetic knee brake 210 further comprises an extension stop system or assembly. The extension stop system controls the maximum allowable extension angle by physically limiting the rotation between the outer side forks 236, 238 and the outer spline 232, and hence the rotation of the knee joint.

In one preferred embodiment, the prosthetic knee brake 210 further comprises an extension assist to help straighten the leg by urging or biasing the leg to extension by applying a controlled torque or force. Any one of a number of devices, such as a spring-loaded extension assist, as known in the art may be used in conjunction with the present invention.

In one preferred embodiment, the prosthetic knee brake 210 comprises forty rotors 220 and forty one stators 230 interspersed in an alternating fashion. This results in forty flux interfaces or fluid gaps in which the magnetorheological (MR) fluid resides. In another preferred embodiment, the number of rotors 220 is about ten to one hundred, the number of stators 230 is about eleven to one hundred one so that the number of MR fluid to rotor interfaces which produce braking in the presence of a magnetic field is twice the number of rotors. In yet another preferred embodiment, the number of rotors 220 is in the range of one to one hundred. In a further preferred embodiment, the number of stators 230 is in the range of one to one hundred. In other preferred embodiments, the number of rotors 220, stators 230 and/or flux interfaces may be alternately selected with efficacy, as needed or desired, giving due consideration to the goals of providing a wide dynamic torque range, and/or of achieving one or more of the benefits and advantages as taught or suggested herein.

Advantageously, the induced yield stress or viscous torque is proportional to the overlap area between a rotor-stator pair multiplied by twice the number of rotors (the number of MR fluid to rotor interfaces which produce braking torque in the presence of a magnetic field). This desirably allows the viscous torque or yield stress to be increased or decreased by selecting or predetermining the number of rotors 220 and/or stators 230 and/or the overlap or mating surface area between adjacent rotors 220 and/or stators 230. Another advantage is that this permits control over the overall size, that is radial size and lateral size, of the MR actuated prosthetic brake 210. For example, the overall knee configuration may be made radially larger and laterally slimmer while providing the same viscous torque range by appropriate selection of the number of flux interfaces and the overlap area of the shearing surfaces.

It is desirable to minimize the MR fluid gap between adjacent rotors 220 and stators 230 since the power needed to saturate the total MR fluid gap is a strong function of the gap size. Thus, advantageously, a smaller gap size renders the MR actuated brake 210 more efficient and reduces power consumption.

Preferably, the MR fluid gap size is also selected so that in the absence of an applied magnetic field only a viscous damping force or torque component is present from the shearing of MR fluid between adjacent rotor and stator surfaces. That is, there is no frictional torque component between the rotors 220 and stators 230 under zero-field conditions.

Accordingly, in one preferred embodiment, the power required to saturate the MR fluid is lowered and the dynamic range of the knee is enhanced by minimizing the MR fluid gap size. In this embodiment, the gap is not reduced so much that, under zero-field conditions, a normal force acts between adjacent rotor and stator surfaces, causing frictional rubbing. The absence of friction between rotors and stators enables the knee joint to swing freely, thereby providing a wider dynamic range. As a note, the viscous damping at zero-field does not increase dramatically with decreasing fluid gap because the MR fluid exhibits a property known as shear rate thinning in which fluid viscosity decreases with increasing shear rate.

In one preferred embodiment, the MR fluid gap size or width between adjacent rotors 220 and stators 230 is about 40 microns ($\mu$m) or less. In another preferred embodiment, the MR fluid gap size or width between adjacent rotors 220 and stators 230 is in the range from about 10 $\mu$m to about 100 $\mu$m. In other preferred embodiments, the MR fluid gap size can be alternately dimensioned and/or configured with efficacy, as required or desired, giving due consideration to the goals of providing an energy efficient prosthetic knee actuator 210 having a wide dynamic torque range, and/or of achieving one or more of the benefits and advantages as taught or suggested herein.

The electronically controlled magnetorheologically actuated prosthetic knee brake of the preferred embodiments provides high-speed instantly responsive control of knee movement, yet is robust and affordable for the amputee. The preferred embodiments advantageously provide improved stability, gait balance and energy efficiency for amputees and simulate and/or closely recreate the dynamics of a natural knee joint.

During operation, the electromagnet or magnetic coil 214 is actuated, as needed, by a selected or predetermined electrical signal, voltage or current to generate an active variable magnetic field passing substantially perpendicularly to the plurality of rotor and stator surfaces and through the MR fluid or film between adjacent rotors 220 and stators 230 to generate a variable damping torque (or rotary resistive force) which precisely and accurately controls the rotary motion of the prosthetic knee 210. As discussed above, in accordance with one preferred embodiment, the torque comprises a frictional damping component.

Desirably, the MR actuated prosthetic knee 210 of the preferred embodiments provides a rapid and precise response. The materials in MR particles respond to the applied magnetic field within milliseconds, thereby allowing for real-time control of the fluid rheology and the knee motion. This facilitates in permitting the patient to move in a safe and/or more natural manner.

Advantageously, the viscous damping torque is generated by shearing of the MR fluid. Hence, there is no or negligible pressure build-up or change within the MR actuated prosthetic knee 210 of the present invention. This substantially eliminates or reduces the chances of fluid leakage and failure of the knee, and hence desirably adds to the safety. Moreover, costly and/or relatively complex components such as pressure bearings and the like need not be utilized to provide a reliable seal.

Another advantage is that the plurality of shearing surfaces or flux interfaces between adjacent rotors 220 and stators 230 behave like a torque multiplier and allow the viscous torque level (and/or frictional torque) to be stepped up to a desired maximum value without the use of an additional transmission or other auxiliary component. Moreover, the flexibility in selecting the overlap surface area between adjacent rotors 220 and stators 230 can also increase or decrease the maximum attainable viscous torque (and/or frictional torque). Thus, desirably a wide dynamic torque or torsional resistance range can be provided, as needed or desired, which adds to the versatility of the invention without adding substantially to system size, weight and complexity.

In one preferred embodiment, the prosthetic knee actuator of the preferred embodiments provides a maximum dynamic torque of about 40 Newton-meters (N-m). In another preferred embodiment, the prosthetic knee actuator of the preferred embodiments provides a dynamic torque in the range from about 0.5 N-m to about 40 N-m. In yet another preferred embodiment, the prosthetic knee actuator of the preferred embodiments provides a dynamic torque in the range from about 1 N-m to about 50 N-m. In other preferred embodiments, the prosthetic knee actuator can provide other dynamic torque ranges with efficacy, as needed or desired, giving due consideration to the goals of achieving one or more of the benefits and advantages as taught or suggested herein.

Also advantageously, the optimized thinness of the MR fluid gap between adjacent rotors 220 and stators 230 provides a higher maximum torque, a wider dynamic torque range and requires less energy consumption, preferably about 10 Watts or less. This adds to the efficiency and practicality of the MR actuated prosthetic brake 210 of the preferred embodiments and also saves on cost since a lower wattage and/or less complex power source can be used.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A method of controlling a prosthetic knee system, comprising:
   measuring at least one characteristic of knee movement;
   calculating a damping value based at least partly on the at least one measured characteristic; and
   applying the damping value to control a resistance of a magnetorheological damper operating primarily in shear mode, wherein said damping is created primarily by shear forces.

2. The method of claim 1, wherein the magnetorheological damper operating primarily in shear mode comprises a rotary magnetorheological damper operating primarily in shear mode.

3. The method of claim 1, wherein the measuring comprises receiving a value from a knee angle sensor.

4. The method of claim 1, wherein the measuring comprises receiving a value from a load sensor.

5. The method of claim 4, wherein receiving a value from the load sensor comprises receiving at least one value from a strain gauge.

6. The method of claim 1, wherein the calculating comprises adapting a damping parameter.

7. The method of claim 1, further comprising identifying a control state based at least partly on the at least one measured characteristic of knee movement, and calculating a damping value based at least partly on the control state.

8. A prosthetic knee system, comprising:
   a magnetorheological damper configured to provide damping to a prosthetic knee, wherein said damping is created primarily by shear forces;
   at least one sensor configured to measure knee motion; and
   a software system configured to send a control signal to the damper based at least partly on the knee motion measured by the at least one sensor.

9. The system of claim 8, wherein the magnetorheological damper comprises a rotary magnetorheological damper.

10. The system of claim 8, wherein the at least one sensor comprises a knee angle sensor.

11. The system of claim 8, wherein the at least one sensor comprises a load sensor.

12. The system of claim 11, wherein the load sensor comprises at least one strain gauge.

13. The system of claim 8, wherein the control signal comprises a current and wherein the damper is configured to vary resistance to rotation in response to the current.

14. The system of claim 8 wherein the software system is configured to identify a control state based at least partly on the measure of knee motion and configured to send a control signal to the damper based at least partly on the control state.

15. A method of controlling a prosthetic joint system, comprising:
   measuring at least one characteristic of joint movement;
   identifying a control state from a plurality of distinct, predetermined control states based at least partly on the at least one measured characteristic of joint movement;
   calculating a damping value based at least partly on the control state; and
   applying the damping value to control a resistance of a magnetorheological damper, wherein said damping is created primarily by shear forces.

16. The method of claim 15, wherein each of the predetermined control states corresponds to a phase of the gait.

17. The method of claim 15, wherein the prosthetic joint system comprises a prosthetic knee.

18. The method of claim 17, wherein the magnetorheological damper operates primarily in shear mode.

19. The method of claim 15, wherein the measuring comprises receiving a value from an angle sensor.

20. The method of claim 15, wherein the measuring comprises receiving a value from a load sensor.

21. The method of claim 15, wherein the calculating comprises adapting a damping parameter.

22. A prosthetic joint system, comprising:
 a magnetorheological damper configured to provide damping to a prosthetic joint, wherein said damping is created primarily by shear forces;
 at least one sensor configured to measure joint motion; and
 a software system configured to identify a control state from a plurality of distinct, predetermined control states based at least partly on the measure of joint motion and configured to send a control signal to the damper based at least partly on the control state.

23. The system of claim 22, wherein each of the predetermined control states corresponds to a phase of the gait.

24. The system of claim 22, comprising a prosthetic knee.

25. The system of claim 22, wherein the magnetorheological damper operates primarily in shear mode.

26. The system of claim 22, wherein the at least one sensor comprises an angle sensor.

27. The system of claim 22, wherein the at least one sensor comprises a load sensor.

28. The system of claim 22, wherein the control signal comprises a current and wherein the damper is configured to vary resistance to rotation in response to the current.

* * * * *

UNITED STATES PATENT AND TRADEMARK OFFICE
CERTIFICATE OF CORRECTION

| | | |
|---|---|---|
| PATENT NO. | : 7,279,009 B2 | Page 1 of 1 |
| APPLICATION NO. | : 10/646097 | |
| DATED | : October 9, 2007 | |
| INVENTOR(S) | : Hugh M. Herr et al. | |

It is certified that error appears in the above-identified patent and that said Letters Patent is hereby corrected as shown below:

On page 2, column 2 (Foreign Patent Documents), line 15, after "GB 2244006 A" please delete "11/2001" and insert --11/1991--, therefor.

On page 2, column 2 (Other Publications), line 5, delete "Artifical" and insert --Artificial--, therefor.

At column 4, line 39, after "muscles" insert --(--.

At column 5, line 3, delete "60°°" and insert --60°--, therefor.

At column 5, line 56, delete "toeoff" and insert --toe off--, therefor.

At column 5, line 64, after "during" insert --the--.

At column 5, line 67, after "brake in" delete "the" and insert --a--, therefor.

At column 8, line 29, delete "EEProm" and insert --EEPROM--, therefor.

At column 8, line 38, delete "ethernet" and insert --Ethernet--, therefor.

At column 28, line 49, in claim 14, after "claim 8" insert --,--.

Signed and Sealed this

Seventeenth Day of March, 2009

JOHN DOLL
*Acting Director of the United States Patent and Trademark Office*